United States Patent
Jung et al.

(10) Patent No.: US 9,530,970 B2
(45) Date of Patent: *Dec. 27, 2016

(54) BENZIMIDAZOLE COMPOUND, ORGANIC PHOTOELECTRIC DEVICE INCLUDING THE SAME, AND DISPLAY ELEMENT INCLUDING THE SAME

(71) Applicants: Sung-Hyun Jung, Uiwang-si (KR); Hyung-Sun Kim, Uiwang-si (KR); Young-Hoon Kim, Uiwang-si (KR); Ho-Jae Lee, Uiwang-si (KR); Seung-Gyoung Lee, Uiwang-si (KR); Eun-Sun Yu, Uiwang-si (KR); Mi-Young Chae, Uiwang-si (KR)

(72) Inventors: Sung-Hyun Jung, Uiwang-si (KR); Hyung-Sun Kim, Uiwang-si (KR); Young-Hoon Kim, Uiwang-si (KR); Ho-Jae Lee, Uiwang-si (KR); Seung-Gyoung Lee, Uiwang-si (KR); Eun-Sun Yu, Uiwang-si (KR); Mi-Young Chae, Uiwang-si (KR)

(73) Assignee: Cheil Industries, Inc., Gumi-Si, Kyeongsangbuk-do (KR)

( * ) Notice: Subject to any disclaimer, the term of this patent is extended or adjusted under 35 U.S.C. 154(b) by 708 days.

This patent is subject to a terminal disclaimer.

(21) Appl. No.: 13/892,604

(22) Filed: May 13, 2013

(65) Prior Publication Data

US 2013/0256641 A1 Oct. 3, 2013

Related U.S. Application Data

(63) Continuation of application No. 13/086,640, filed on Apr. 14, 2011, now abandoned, which is a
(Continued)

(30) Foreign Application Priority Data

Oct. 14, 2008 (KR) .................. 10-2008-0100726

(51) Int. Cl.
*H01L 51/50* (2006.01)
*H01L 51/00* (2006.01)
(Continued)

(52) U.S. Cl.
CPC ......... *H01L 51/0072* (2013.01); *C07D 235/18* (2013.01); *C07D 401/14* (2013.01);
(Continued)

(58) Field of Classification Search
CPC ... C07D 235/18; C07D 401/14; C07D 403/10; C07D 403/14; C09B 57/00; C09B 57/008; C09B 11/06; C09B 2211/1466; H04L 51/0003; H04L 51/0037; H04L 51/0072; H04L 51/0081; H04L 51/0085
See application file for complete search history.

(56) References Cited

U.S. PATENT DOCUMENTS 7,695,828 B2 * 4/2010 Seo .................. C09K 11/06 313/504
8,772,632 B2 * 7/2014 In ..................... C07D 403/10 136/256
(Continued)

FOREIGN PATENT DOCUMENTS

| CN | 1918947 A | 2/2007 |
| CN | 101262044 A | 9/2008 |

(Continued)

OTHER PUBLICATIONS

P.K. Dubey, et al.; "Synthesis of 1-alkyl-2-(substituted-2-pyridyl)benzimidazoles"; Indian Journal of Chemistry, vol. 42B, Sep. 2003, pp. 2115-2118.
(Continued)

*Primary Examiner* — Dawn Garrett
(74) *Attorney, Agent, or Firm* — Lee & Morse, P.C.

(57) ABSTRACT

A benzimidazole compound, an organic photoelectric device, and a display element, the benzimidazole compound
(Continued)

being represented by the following Chemical Formula 1:

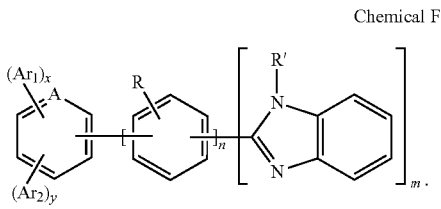

Chemical Formula 1

12 Claims, 9 Drawing Sheets

Related U.S. Application Data continuation of application No. PCT/KR2009/005911, filed on Oct. 14, 2009.

(51) Int. Cl.
| | |
|---|---|
| C07D 235/18 | (2006.01) |
| C07D 401/14 | (2006.01) |
| C07D 403/10 | (2006.01) |
| C07D 403/14 | (2006.01) |
| C09K 11/06 | (2006.01) |
| C09B 57/00 | (2006.01) |

(52) U.S. Cl.
CPC ......... *C07D 403/10* (2013.01); *C07D 403/14* (2013.01); *C09B 57/00* (2013.01); *C09B 57/008* (2013.01); *C09K 11/06* (2013.01); C09K 2211/1466 (2013.01); H01L 51/0003 (2013.01); H01L 51/0037 (2013.01); H01L 51/0081 (2013.01); H01L 51/0085 (2013.01)

(56) References Cited

U.S. PATENT DOCUMENTS

| | | |
|---|---|---|
| 2004/0023060 A1 | 2/2004 | Kim et al. |
| 2004/0170863 A1 | 9/2004 | Kim et al. |
| 2005/0065094 A1 | 3/2005 | Davidai |
| 2005/0186445 A1 | 8/2005 | Zheng et al. |
| 2006/0234946 A1 | 10/2006 | Davidai |
| 2007/0108892 A1 | 5/2007 | Bae et al. |
| 2007/0131929 A1 | 6/2007 | Bae et al. |
| 2007/0205412 A1 | 9/2007 | Bae et al. |
| 2007/0247059 A1 | 10/2007 | Cho et al. |
| 2007/0257600 A1 | 11/2007 | Matsuura et al. |
| 2007/0262706 A1 | 11/2007 | Yoon et al. |
| 2007/0267970 A1 | 11/2007 | Yamamoto et al. |
| 2008/0079356 A1 | 4/2008 | Park et al. |
| 2008/0093982 A1 | 4/2008 | Cho et al. |
| 2008/0100207 A1 | 5/2008 | Park et al. |
| 2008/0233387 A1 | 9/2008 | Kambe et al. |
| 2008/0278072 A1 | 11/2008 | Noh et al. |
| 2008/0284322 A1 | 11/2008 | Hosokawa et al. |
| 2008/0303414 A1 | 12/2008 | Cho et al. |
| 2009/0134783 A1 | 5/2009 | Lin et al. |
| 2009/0200542 A1 | 8/2009 | Cho et al. |
| 2010/0045170 A1 | 2/2010 | Lee et al. |
| 2010/0071769 A1 | 3/2010 | Bae et al. |
| 2013/0075705 A1* | 3/2013 | Takasu ............... C07D 403/14 257/40 |

FOREIGN PATENT DOCUMENTS

| | | |
|---|---|---|
| EP | 2100941 A2 | 9/2009 |
| JP | 59-075257 | 4/1984 |
| JP | 10-106749 A | 4/1998 |
| JP | 2001-247858 | 9/2001 |
| JP | 2002-249765 A | 9/2002 |
| JP | 2003-313546 A | 11/2003 |
| JP | 2004-292766 A | 10/2004 |
| JP | 2004-352655 A | 12/2004 |
| JP | 2005-089543 A | 4/2005 |
| JP | 2007-269772 A | 10/2007 |
| JP | 2007-277306 A | 10/2007 |
| JP | 2009-158848 A | 7/2009 |
| KR | 10-2006-0114001 A | 11/2006 |
| KR | 10-2007-0043666 A | 4/2007 |
| KR | 10-2007-0062920 A | 6/2007 |
| KR | 10-2008-0031931 A | 4/2008 |
| KR | 10-2008-0039057 A | 5/2008 |
| KR | 10-2008-0051506 A | 6/2008 |
| KR | 10-2008-0082473 A | 9/2008 |
| KR | 10-0910150 B1 | 7/2009 |
| KR | 2009-0073850 A | 7/2009 |
| KR | 2009073852 A * | 7/2009 |
| WO | WO 02/088274 A1 | 7/2002 |
| WO | WO-03/050201 A1 | 6/2003 |
| WO | WO 2005/023250 A1 | 3/2005 |
| WO | WO-2005/076669 A1 | 8/2005 |
| WO | WO 2005/076669 A1 | 8/2005 |
| WO | WO 2006/080640 A1 | 8/2006 |
| WO | WO 2007/018007 A1 | 2/2007 |
| WO | WO 2007/046658 A1 | 4/2007 |
| WO | WO-2007/069847 A1 | 6/2007 |
| WO | WO-2007/102683 A1 | 9/2007 |
| WO | WO 2007/111262 A1 | 10/2007 |
| WO | WO 2008/069586 A1 | 6/2008 |
| WO | WO 2008/133483 A2 | 11/2008 |
| WO | WO 2009/084544 A1 | 7/2009 |

OTHER PUBLICATIONS

Tang, et al.; Organic electroluminescent diodes; Applied Physics Letters; Sep. 21, 1987; pp. 913-915; vol. 51, No. 12; American Institute of Physics; United States.

O'Brien, et al.; Improved energy transfer in electrophosphorescent devices; Applied Physics Letters; Jan. 18, 1999; pp. 442-444; vol. 74, No. 3; American Institute of Physics; United States.

Katritzky, et al.; A 1,4-Photochemical Aryl Shift; Tetrahedron Letters, 1982; pp. 1241-1242; vol. 23, No. 12; Pergamon Press, Ltd.; Great Britain.

Petroud, et al.; Luminescent Properties of Lanthanide Nitrato Complexes with Substituted Bis(benzimidazolyl)pyridines; Inorganic Chemistry; 1997; pp. 1345-1353; vol. 36, No. 7; American Chemical Society; USA.

Dubey, et al.: Synthesis of 1-Alkyl-2-(substituted-2-pyridyl)benzimidazoles; Indian Journal of Chemistry; 2003; pp. 2115-2118 (Abstract); Section B; Organic Chemistry Including Med. Chemistry 42, No. 9; Department of Chemistry, JNT University; India.

Huang et al.; Highly Phosphorescent Bis-Cyclometalated Iridium Complexes Containing Benzoimidazole-Based Ligands; Chem. Mater.; 2004; pp. 2480-2488; vol. 16, No. 12; American Chemical Society; USA.

Stibrany et al.; A Geometrically Constraining Bis(benzimidazole) Ligand and Its Nearly Tetrahedral Complexes with Fe(II) and Mn(II); Inorganic Chemistry; 2004; pp. 1472-1480; vol. 43, No. 4; American Chemical Society; USA.

Lai et al.; Benzimidazole/Amine-Based Compounds Capable of Ambipolar Transport for Application for Single-Layer Blue-Emitting OLEDs and as Hosts for Phosphorescent Emitters; Angewante Chemie Int. Ed.; 2008; pp. 581-585; vol. 47; Wiley-VCH Verlag GmbH & Co. KGaA Weinheim, Germany.

Ke et al.; High efficiency blue light emitting unipolar transistor incorporating multifunctional electrodes; Applied Physics Letters; 2009; pp. 153307-1-1533707-3; vol. 94; American Institute of Physics; USA.

Ke et al.; Single molecule color controllable light emitting organic field effect transistors for white light emission with high color

(56) References Cited

OTHER PUBLICATIONS stability; Applied Physics Letters; 2009; pp. 063303-1-063303-3; vol. 95; American Institute of Physics; USA.

Lai, M., et al., "Benzimidazole/Amine-Based Compounds Capable of Ambipolar Transport for Application in Single-Layer Blue-Emitting OLEDs and as Hosts for Phosphorescent Emitters," *Angewandte Chemie*, vol. 120, Issue 3, Jan. 4, 2008, pp. 591-595.

Baldo, M. A., et al., "Very high-efficiency green organic light-emitting devices based on electrophosphorescence," *Applied Physics Letters*, vol. 75, No. 1, Jul. 5, 1999, pp. 4-6.

USPTO Action mailed Oct. 15, 2013, in U.S. Appl. No. 13/915,802 (commonly-owned), wherein claims were provisionally rejected on the ground of nonstatutory double patenting over claims of the captions application.

\* cited by examiner

BENZIMIDAZOLE COMPOUND, ORGANIC PHOTOELECTRIC DEVICE INCLUDING THE SAME, AND DISPLAY ELEMENT INCLUDING THE SAME

CROSS-REFERENCE TO RELATED APPLICATION

This application is a continuation of pending application Ser. No. 13/086,640, filed Apr. 14, 2011, which in turn is a continuation of International Application No. PCT/KR2009/005911, entitled "Benzimidazole Compounds and Organic Photoelectric Device with the Same," which was filed on Oct. 14, 2009, the entire contents of which are hereby incorporated by reference.

BACKGROUND

1. Field

Embodiments relate to a benzimidazole compound, an organic photoelectric device including the same, and a display element including the same.

2. Description of the Related Art

An organic photoelectric device has been highlighted for the next generation display device. The organic photoelectric device may be used in a display element or device driven at a low voltage, and may have various advantages over a thin film transistor-liquid crystal display (TFT-LCD). For example, the organic photoelectric device may be used in a display element or device that may be thinner, may have a wide viewing angle, and may have rapid response speed. A small or medium sized display element or device including an organic photoelectric device may also have an equivalent or better image quality compared to a TFT-LCD, and its manufacturing process may be very simple. Therefore, it is considered that it will be advantageous in terms of cost in the future.

An organic photoelectric device includes an organic light emitting material between a rear plate (including ITO transparent electrode patterns as an anode on a transparent glass substrate) and an upper plate (including a metal electrode as a cathode on a substrate). When a predetermined voltage is applied between the transparent electrode and the metal electrode, current flows through the organic light emitting material to emit light.

Generally, an organic photoelectric device is composed of an anode of a transparent electrode, an organic thin layer as a light emitting region, and a metal electrode (cathode) formed on a glass substrate, in that order. The organic thin layer may include, e.g., an emission layer, a hole injection layer (HIL), a hole transport layer (HTL), an electron transport layer (ETL), and/or an electron injection layer (EIL). It may further include an electron blocking layer or a hole blocking layer due to the emission characteristics of the emission layer.

When an electric field is applied to the organic light emitting diode, the holes and electrons are injected from the anode and the cathode, respectively. The injected holes and electrons are recombined on the emission layer though the hole transport layer (HTL) and the electron transport layer (ETL) to provide light emitting excitons. The provided light emitting excitons produce light by transiting to the ground state.

The light emission layer material may be classified as a fluorescent material using singlet excitons and a phosphorescent material using triplet excitons according to the light emitting mechanism.

When the triplet exciton is transited, it cannot directly transit to the ground state. Therefore, the electron spin is flipped, and then it is transited to the ground state so that it provides a characteristic of extending the lifetime (emission duration) to more than that of fluorescent emission. In other words, the duration of fluorescent emission is extremely short at several nanoseconds, but the duration of phosphorescent emission is relatively long such as at several microseconds.

In addition, evaluating quantum mechanically, when holes injected from the anode are recombined with electrons injected from the cathode to provide light emitting excitons, the singlet and the triplet are produced in a ratio of 1:3, in which the triplet excitons are produced at three times the amount of the singlet excitons in the organic photoelectric device.

Accordingly, the percentage of the singlet exited state is 25% in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach 100%. When a phosphorescent light emitting material is used, it has advantages in a luminous efficiency of around four times that of the fluorescent light emitting material.

In the above-mentioned organic photoelectric device, a light emitting colorant (dopant) may be added to an emission layer (host) in order to increase the efficiency and stability in the emission state.

SUMMARY

Embodiments are directed to a benzimidazole compound, an organic photoelectric device including the same, and a display element including the same.

The embodiments may be realized by providing a benzimidazole compound represented by the following Chemical Formula 1:

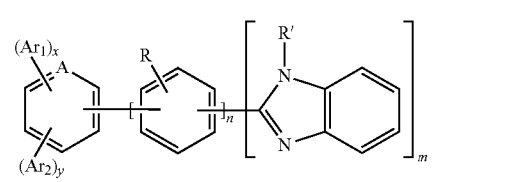

Chemical Formula 1 wherein, in Chemical Formula 1, A is CR" or N wherein R" is hydrogen or a C1 to C10 alkyl, $Ar_1$ to $Ar_2$ are each independently one selected from the group of a substituted or unsubstituted C6 to C30 aryl, a substituted or unsubstituted C2 to C30 heteroaryl, a substituted or unsubstituted C6 to C30 arylamine, a substituted or unsubstituted C2 to C30 heteroarylamine, a substituted or unsubstituted carbazole, and a substituted or unsubstituted fluorene, x and y are each independently an integer of 0 to 5, provided that $1 \leq x+y \leq 5$, R is hydrogen or a C1 to C7 alkyl, n is an integer of 0 to 3, R' is one selected from the group of a substituted or unsubstituted C1 to C50 alkyl and a substituted or unsubstituted C6 to C50 aryl, and m is 1 or 2.

R' in the above Chemical Formula 1 may be a substituted or unsubstituted C6 to C50 aryl.

The benzimidazole compound represented by Chemical Formula 1 may be represented by the following Chemical Formula 2:

Chemical Formula 2

[structure with $(Ar_1)_x$, $(Ar_2)_y$, A, $R'_1$ to $R'_5$, benzimidazole, subscript $m$, subscript $n$]

wherein, in the above Chemical Formula 2, A is CR" or N wherein R" is hydrogen or a C1 to C10 alkyl, $Ar_1$ to $Ar_2$ are each independently one selected from the group of a substituted or unsubstituted C6 to C30 aryl, a substituted or unsubstituted C2 to C30 heteroaryl, a substituted or unsubstituted C6 to C30 arylamine, a substituted or unsubstituted C2 to C30 heteroarylamine, a substituted or unsubstituted carbazole, and a substituted or unsubstituted fluorene, x and y are each independently integers of 0 to 5, provided that $1 \leq x+y \leq 5$, n is an integer of 0 to 3, $R_1'$ to $R_5'$ are each independently one selected from the group of hydrogen, a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, and m is 1 or 2.

$Ar_1$ to $Ar_2$ may each independently be one selected from the group of a substituted or unsubstituted C6 to C30 arylamine and a substituted or unsubstituted carbazole.

$x \geq 1$, $y \geq 1$, one of $Ar_1$ and $Ar_2$ may include a substituted or unsubstituted C6 to C30 arylamine, and another of $Ar_1$ and $Ar_2$ may include a substituted or unsubstituted carbazole.

$Ar_1$ to $Ar_2$ may each independently be represented by one of the following Chemical Formulae 3 to 33:

Chemical Formula 3

[phenyl with $(R_1)_{n_1}$, *]

Chemical Formula 4

[biphenyl with $(R_2)_{n_2}$, $(R_3)_{n_3}$, *]

Chemical Formula 5

[diphenyl ether with $(R_4)_{n_4}$, $(R_5)_{n_5}$, *]

Chemical Formula 6

[diphenyl sulfide with $(R_6)_{n_6}$, $(R_7)_{n_7}$, *]

Chemical Formula 7

[fluorene with $(R_8)_{n_8}$, $(R_9)_{n_9}$, $R_{72}$, $R_{73}$, *]

Chemical Formula 8

[terphenyl with $(R_{10})_{n_{10}}$, $(R_{11})_{n_{11}}$, *]

Chemical Formula 9

[naphthalene with $(R_{12})_{n_{12}}$, $(R_{13})_{n_{13}}$, *]

Chemical Formula 10

[pyrrole with $(R_{14})_{n_{14}}$, $R_{15}$, *]

Chemical Formula 11

[anthracene with $(R_{16})_{n_{16}}$, $(R_{17})_{n_{17}}$, $(R_{18})_{n_{18}}$, *]

Chemical Formula 12

[furan with $(R_{19})_{n_{19}}$, *]

Chemical Formula 13

[thiophene with $(R_{20})_{n_{20}}$, *]

Chemical Formula 14

[stilbene with $(R_{21})_{n_{21}}$, $(R_{22})_{n_{22}}$, *]

-continued
Chemical Formula 15
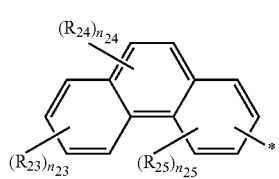
Chemical Formula 16
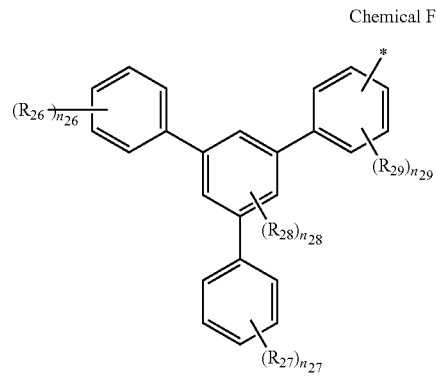
Chemical Formula 17
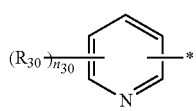
Chemical Formula 18
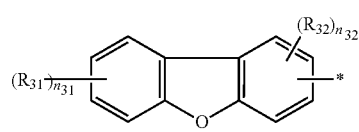
Chemical Formula 19
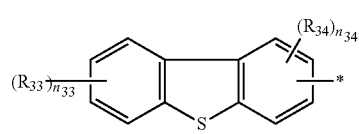
Chemical Formula 20
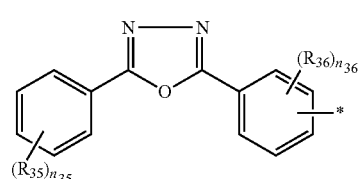
Chemical Formula 21
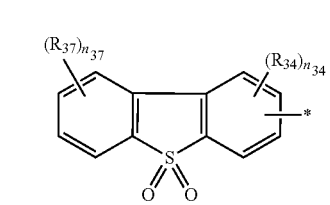
-continued
Chemical Formula 22
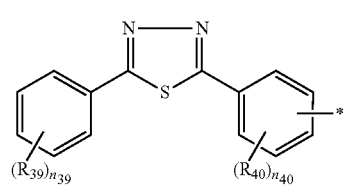
Chemical Formula 23
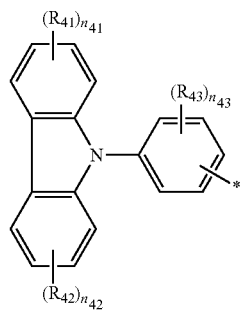
Chemical Formula 24
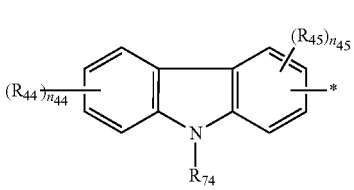
Chemical Formula 25
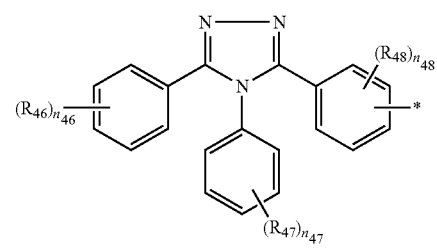
Chemical Formula 26
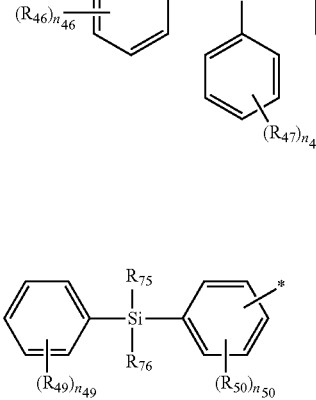
Chemical Formula 27
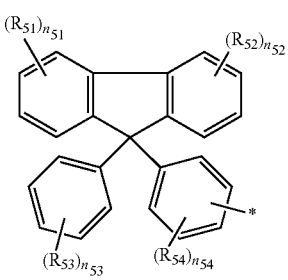

Chemical Formula 28

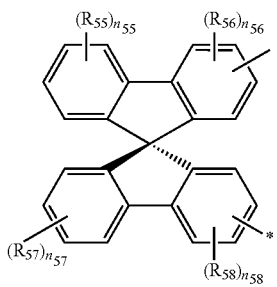

Chemical Formula 29

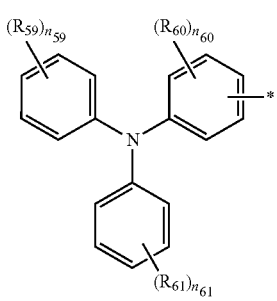

Chemical Formula 30

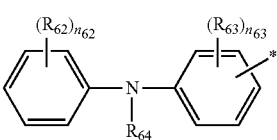

Chemical Formula 31

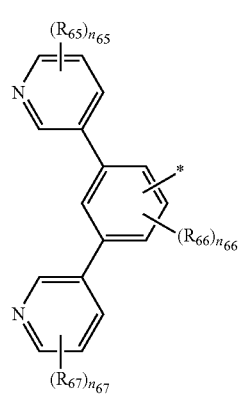

Chemical Formula 32

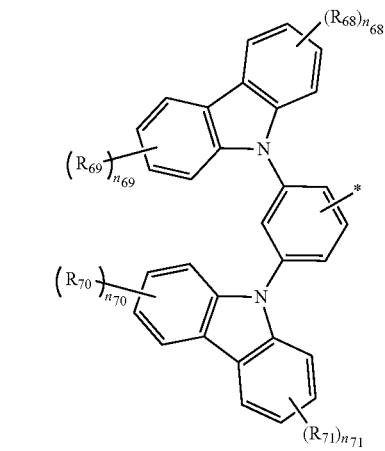

Chemical Formula 33

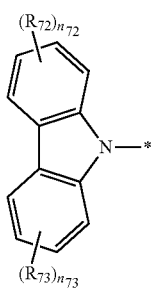

wherein in the above Chemical Formulae 3 to 33, $R_1$ to $R_{76}$ are each independently one selected from the group of a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are each independently integers of 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, and $n_{67}$ to $n_{73}$ are each independently integers of 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ are each independently integers of 0 to 3, and $n_{17}$ and $n_{24}$ are each independently integers of 0 to 2.

The benzimidazole compounds may be a charge transporting material or a host material in an organic photoelectric device.

The benzimidazole compound represented by Chemical Formula 1 may be represented by one of the following Chemical Formulae 34-40:

Chemical Formula 34
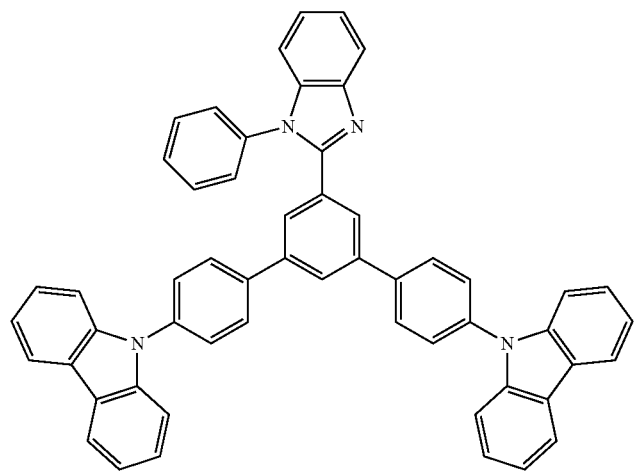
Chemical Formula 35
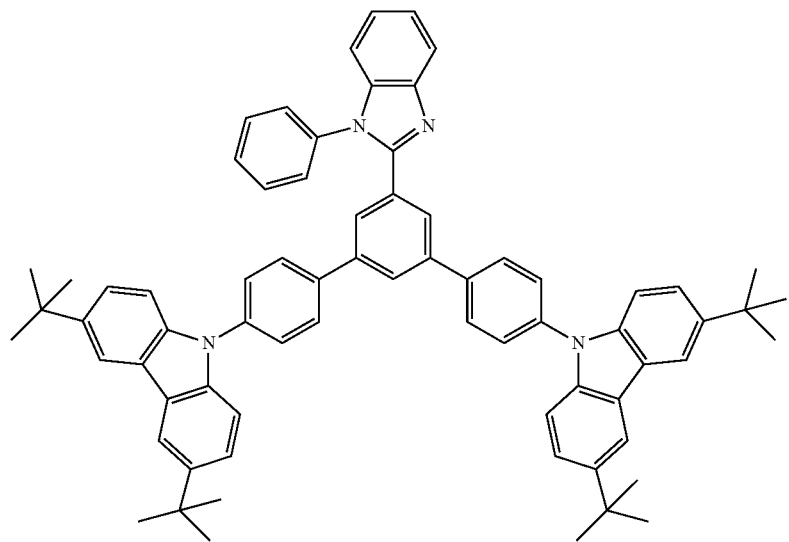
Chemical Formula 36
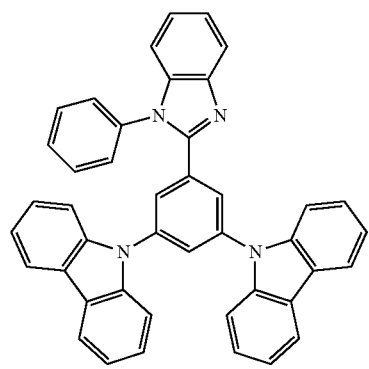
Chemical Formula 37
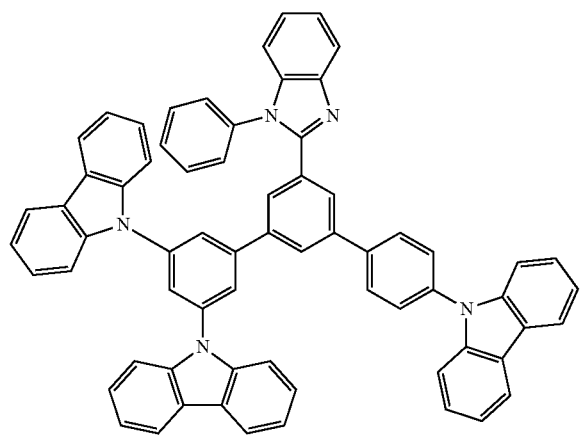

Chemical Formula 38

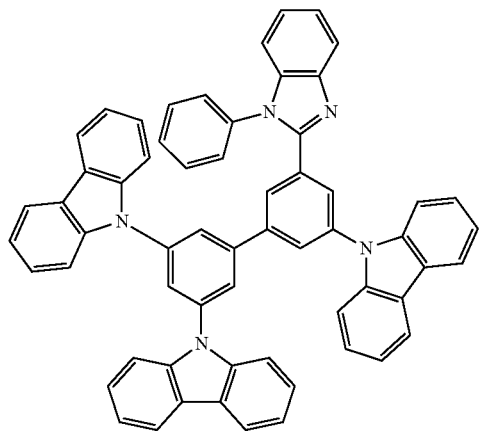

Chemical Formula 39

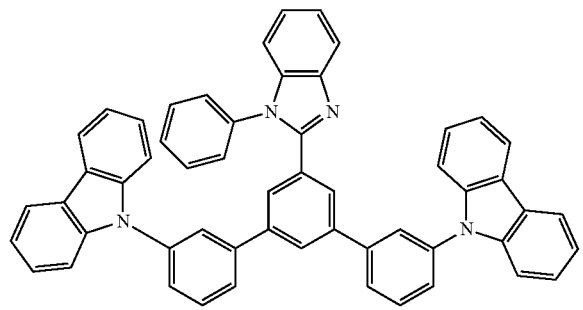

Chemical Formula 40

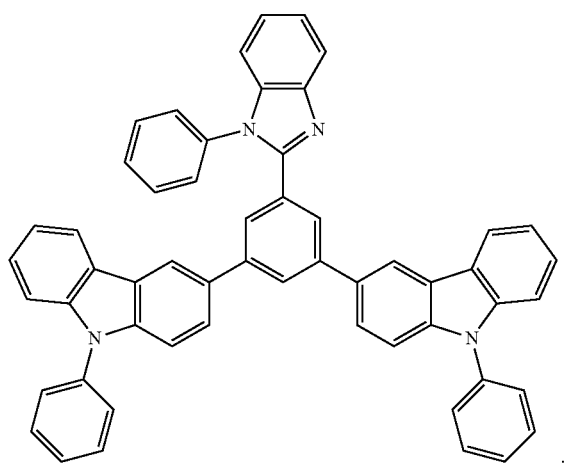

The embodiments may also be realized by providing an organic photoelectric device including an anode, a cathode, and at least one organic thin layer between the anode and cathode, the at least one organic thin layer including the benzimidazole compound of an embodiment.

The at least one organic thin layer may be an emission layer.

The at least one organic thin layer may include at least one of an electron injection layer (EIL), an electron transport layer (ETL), and a hole blocking layer.

The embodiments may also be realized by providing a display element including the organic photoelectric device of an embodiment.

BRIEF DESCRIPTION OF THE DRAWINGS

The embodiments will become more apparent to those of ordinary skill in the art by describing in detail exemplary embodiments with reference to the attached drawings, in which.

DETAILED DESCRIPTION

Figure 1:
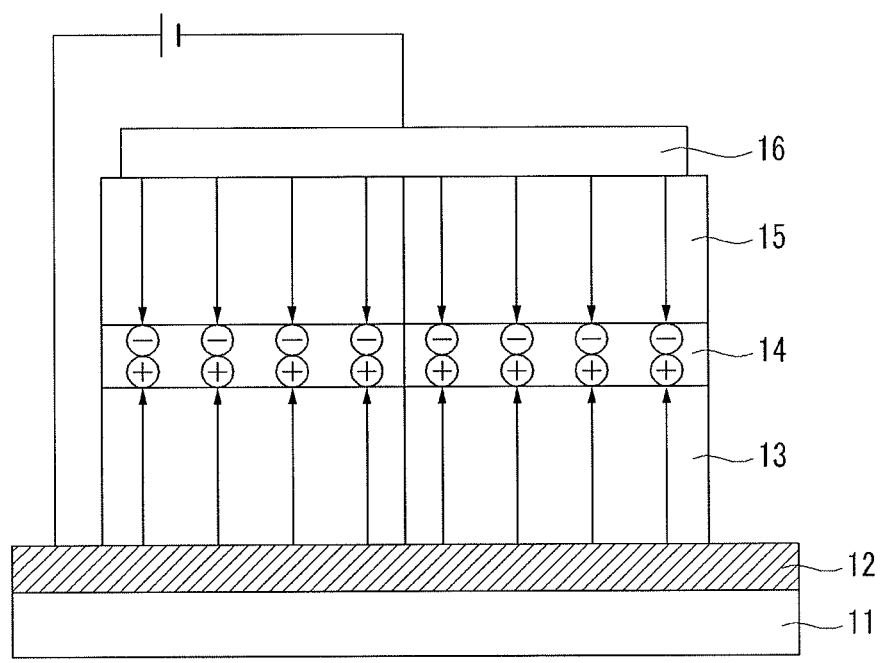
FIG. 1 illustrates a schematic cross-sectional view showing a display element including an organic photoelectric device according to an embodiment.

Korean Patent Application No. 10-2008-0100726, filed on Oct. 14, 2008, in the Korean Intellectual Property Office, and entitled: "Benzimidazole Compounds and Organic Photoelectric Device with the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not provided, the term "substituted" may refer to one substituted with a substituent selected from the group of a halogen, a cyano, a hydroxy, an amino, a nitro, a carboxyl, an azo, a ferro, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl.

As used herein, when specific definition is not provided, the term "hetero" may refer to one including 1 to 3 heteroatoms selected from the group of N, O, S, and P in one ring.

An embodiment provides a benzimidazole compound represented by the following Chemical Formula 1.

[Chemical Formula 1]

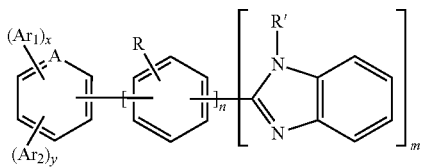

In the above Chemical Formula 1,
A may be C or N,
$Ar_1$ to $Ar_2$ may each independently be selected from the group of a substituted or unsubstituted C6 to C30 aryl, a substituted or unsubstituted C2 to C30 heteroaryl, a substituted or unsubstituted C6 to C30 arylamine, a substituted or unsubstituted C2 to C30 heteroarylamine, a substituted or unsubstituted carbazole, and a substituted or unsubstituted fluorene, x and y may each independently be integers of 0 to 5, provided that 1≤x+y≤5, R may be hydrogen or a lower, e.g., C1 to C7, alkyl,
n may be an integer of 0 to 3,
R' may include one selected from the group of a substituted or unsubstituted C1 to C50 alkyl and a substituted or unsubstituted C6 to C50 aryl, and
m may be 1 or 2.

In the above Chemical Formula 1, R' is preferably a substituted or unsubstituted C6 to C50 aryl. In an implementation, the C6 to C50 aryl may include one selected from the group of a substituted or unsubstituted phenyl and a substituted or unsubstituted naphthyl.

The benzimidazole compound represented by Chemical Formula 1 is preferably represented by the following Chemical Formula 2.

[Chemical Formula 2]

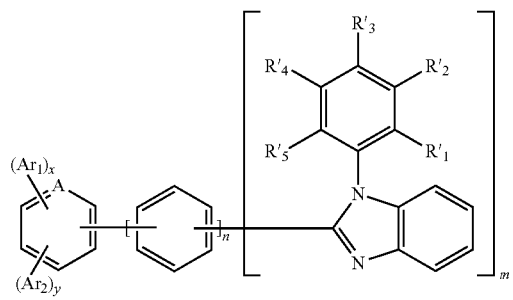

In the above Chemical Formula 2,
A may be C or N,
$Ar_1$ to $Ar_2$ may each independently be one selected from the group of a substituted or unsubstituted C6 to C30 aryl, a substituted or unsubstituted C2 to C30 heteroaryl, a substituted or unsubstituted C6 to C30 arylamine, a substituted or unsubstituted C2 to C30 heteroarylamine, a substituted or unsubstituted carbazole, and a substituted or unsubstituted fluorene, x and y may each independently be integers of 0 to 5, provided that 1≤x+y≤5, n may be an integer of 0 to 3,
$R_1'$ to $R_5'$ may each independently be one selected from the group of hydrogen, a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, and m may be 1 or 2.

As described above, in Chemical Formulae 1 and 2, $Ar_1$ to $Ar_2$ may each independently be one selected from the group of a substituted or unsubstituted C6 to C30 aryl, a substituted or unsubstituted C2 to C30 heteroaryl, a substituted or unsubstituted C6 to C30 arylamine, a substituted or unsubstituted C2 to C30 heteroarylamine, a substituted or unsubstituted carbazole, and a substituted or unsubstituted fluorene.

The substituted or unsubstituted C6 to C30 aryl of Chemical Formulae 1 and 2 preferably includes one selected from the group of a substituted or unsubstituted phenyl, a substituted or unsubstituted tolyl, a substituted or unsubstituted naphthyl, a substituted or unsubstituted anthracenyl, a substituted or unsubstituted terphenyl, a substituted or unsubstituted pyrenyl, a substituted or unsubstituted diphenylanthracenyl, a substituted or unsubstituted dinaphthylanthracenyl, a substituted or unsubstituted pentacenyl, a substituted or unsubstituted bromophenyl, a substituted or unsubstituted hydroxyphenyl, a substituted or unsubstituted stilbene, a substituted or unsubstituted azobenzenyl, and a substituted or unsubstituted ferrocenyl. The substituted or unsubstituted C2 to C30 heteroaryl of Chemical Formulae 1 and 2 preferably includes one selected from the group of a substituted or unsubstituted thienyl and a substituted or unsubstituted pyridyl.

In an implementation, when $Ar_1$ to $Ar_2$ are each independently one selected from the group of a substituted or unsubstituted C6 to C30 arylamine and a substituted or unsubstituted carbazole, the compound may exhibit a desirable balance between electron and hole transporting characteristics.

$Ar_1$ to $Ar_2$ are preferably each independently represented by one of the following Chemical Formulae 3 to 33.

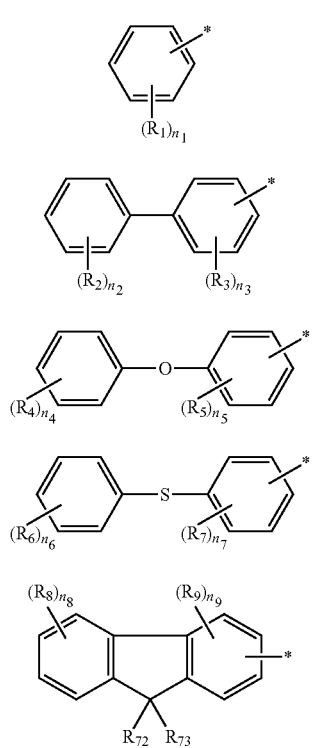

Chemical Formula 3

Chemical Formula 4

Chemical Formula 5

Chemical Formula 6

Chemical Formula 7

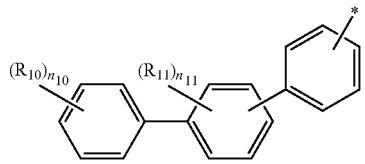

Chemical Formula 8

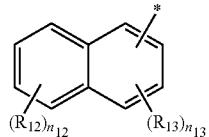

Chemical Formula 9

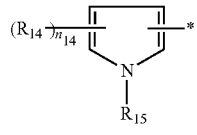

Chemical Formula 10

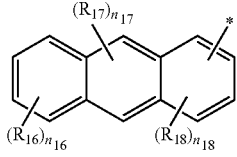

Chemical Formula 11

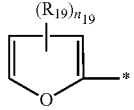

Chemical Formula 12

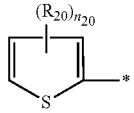

Chemical Formula 13

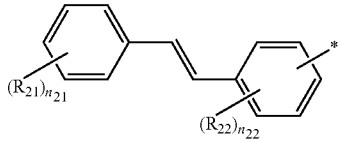

Chemical Formula 14

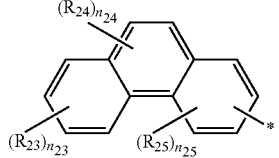

Chemical Formula 15

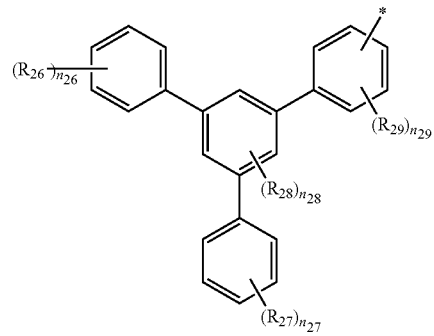

Chemical Formula 16

Chemical Formula 17
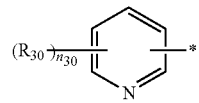
Chemical Formula 18
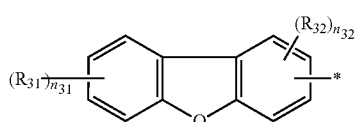
Chemical Formula 19
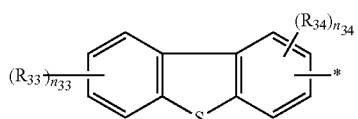
Chemical Formula 20
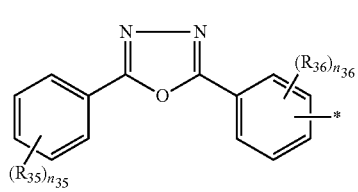
Chemical Formula 21
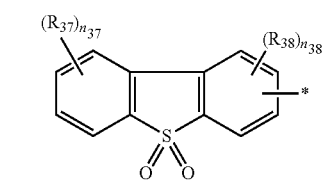
Chemical Formula 22
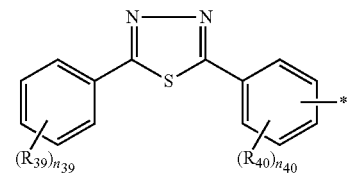
Chemical Formula 23
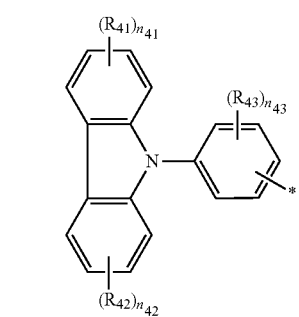
Chemical Formula 24
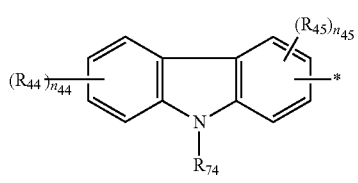
Chemical Formula 25
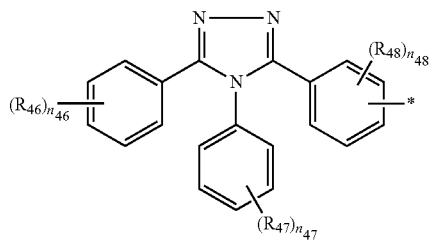
Chemical Formula 26
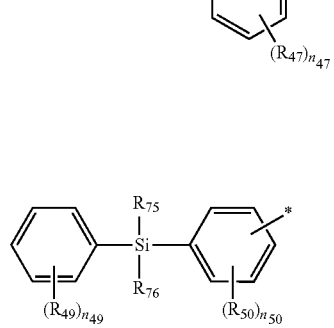
Chemical Formula 27
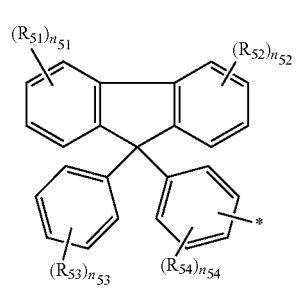
Chemical Formula 28
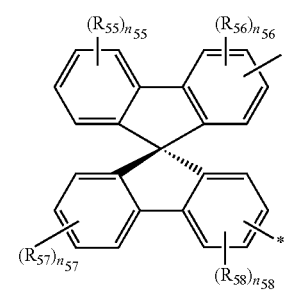
Chemical Formula 29
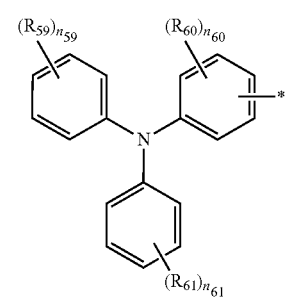
Chemical Formula 30
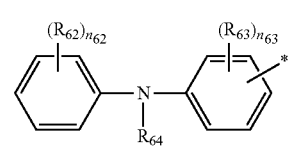

Chemical Formula 31

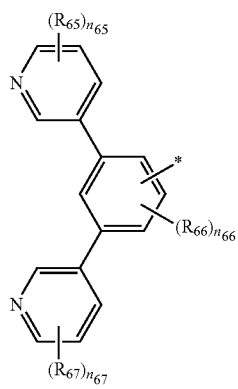

Chemical Formula 33

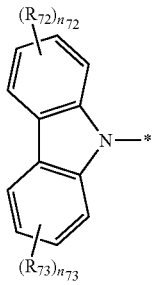

Chemical Formula 32

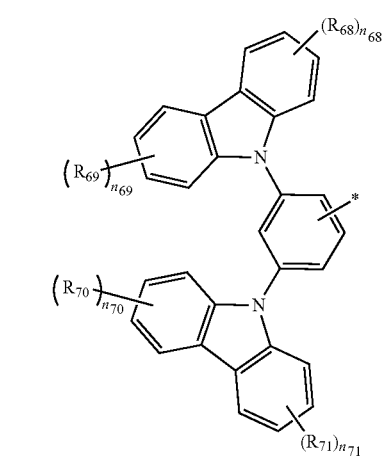

In the above Chemical Formulae 3 to 33, $R_1$ to $R_{76}$ may each independently be one selected from the group of a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ may each independently be integers of 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, and $n_{67}$ to $n_{73}$ may each independently be integers of 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ may each independently be integers of 0 to 3, and $n_{17}$ and $n_{24}$ may each independently be integers of 0 to 2.

The benzimidazole compound represented by Chemical Formula 1, above, preferably includes a compound represented by one of the following Chemical Formulae 34 to 131.

Chemical Formula 34

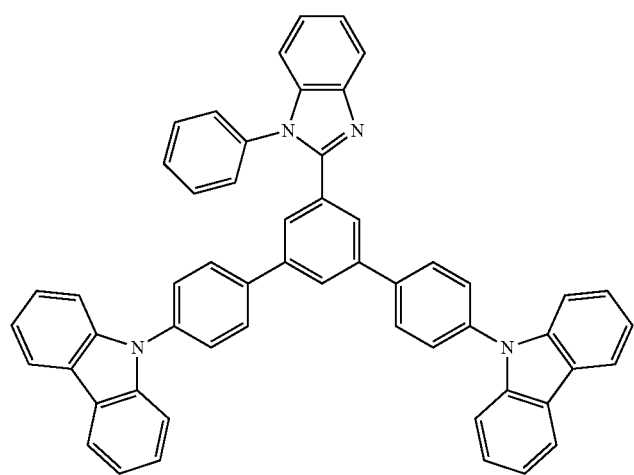

Chemical Formula 35
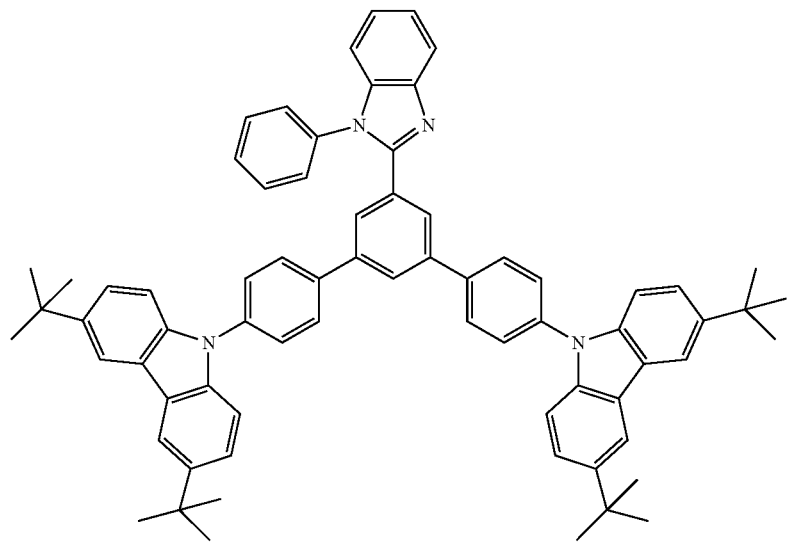
Chemical Formula 36
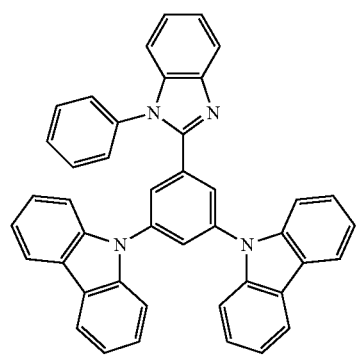
Chemical Formula 37
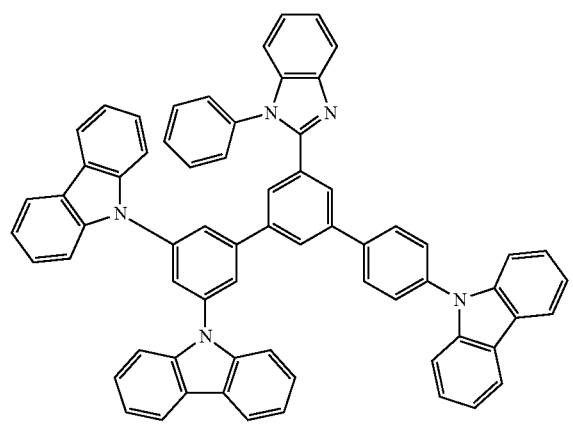
Chemical Formula 38
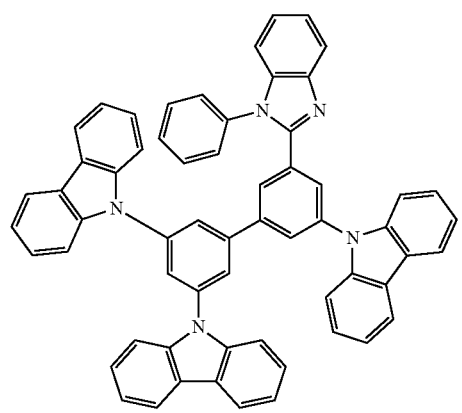
Chemical Formula 39
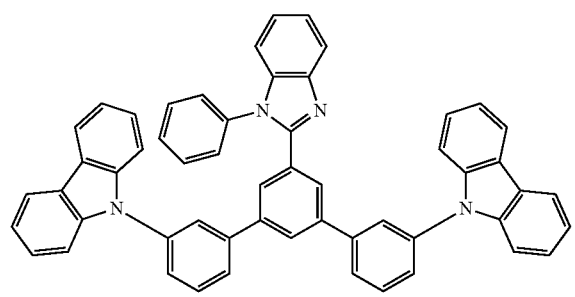

-continued
Chemical Formula 40
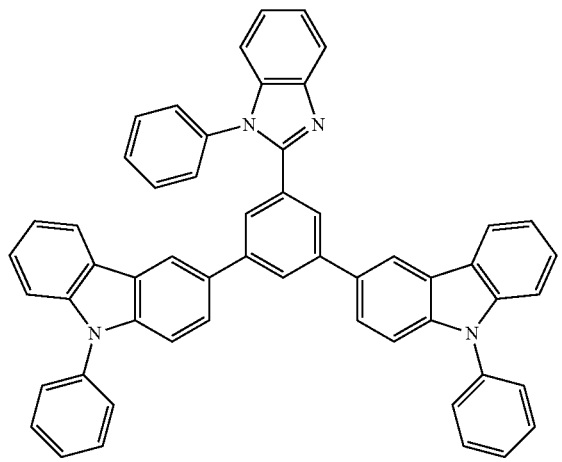
Chemical Formula 41
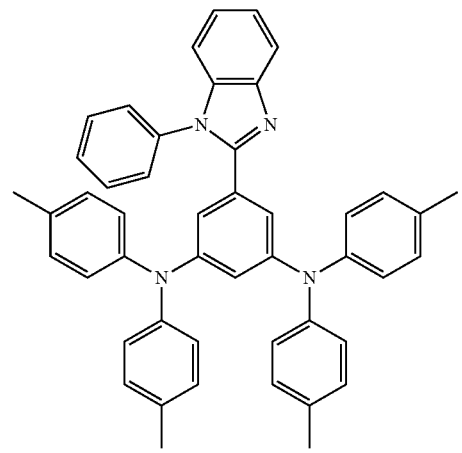
Chemical Formula 42
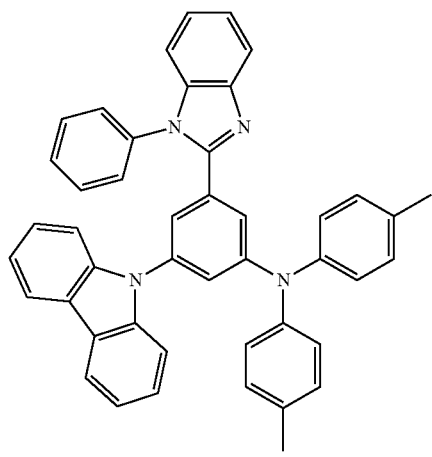
Chemical Formula 43
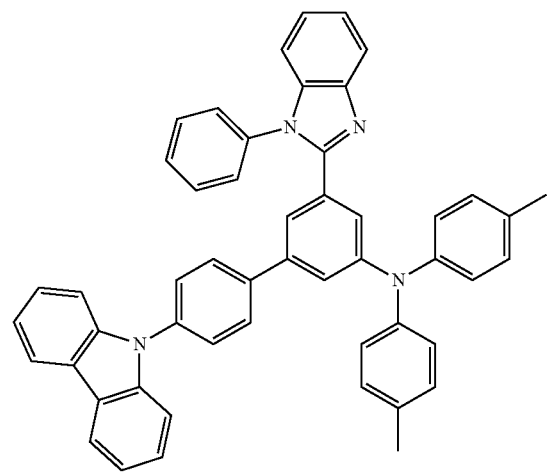
Chemical Formula 44
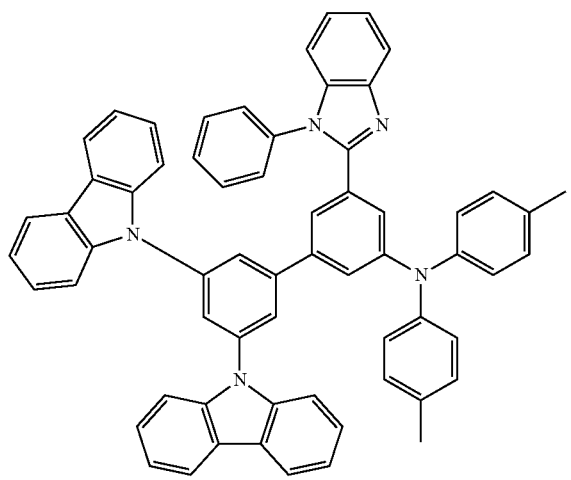
Chemical Formula 45
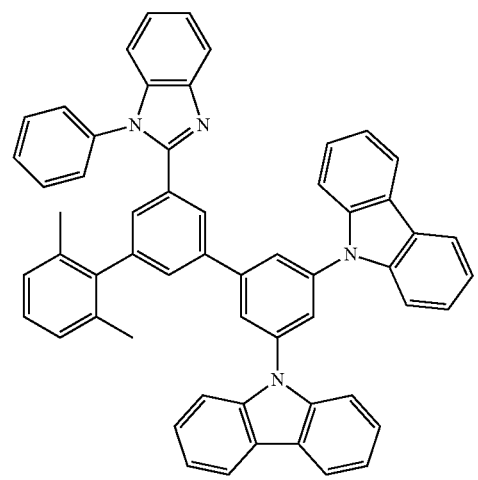

-continued
Chemical Formula 46
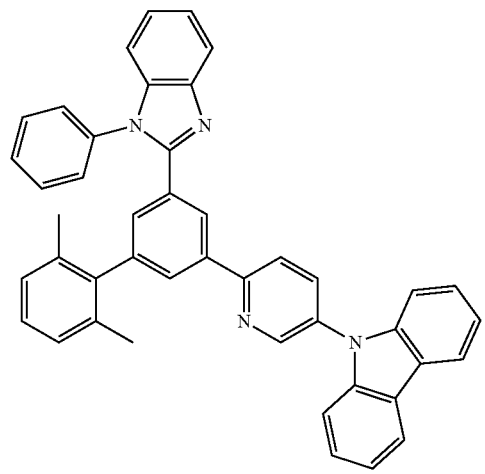
Chemical Formula 47
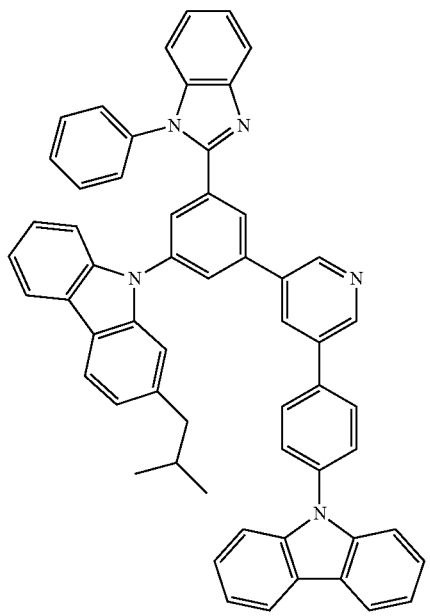
Chemical Formula 48
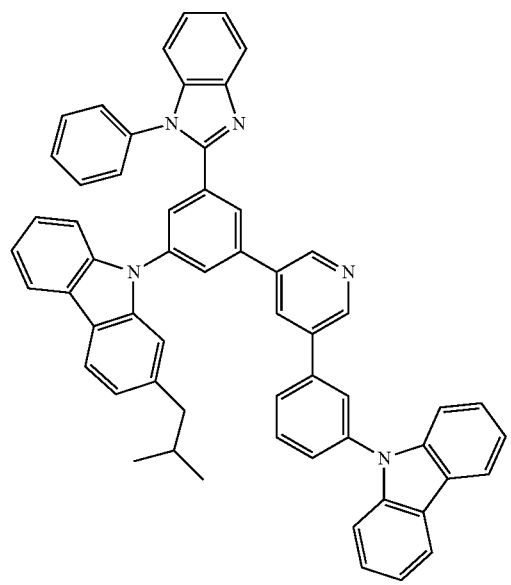
Chemical Formula 49
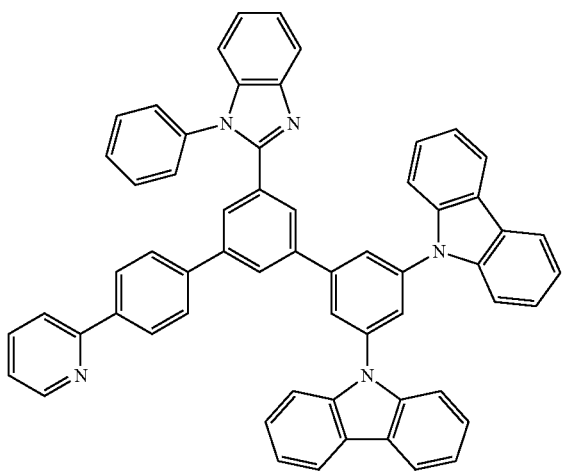

-continued
Chemical Formula 50
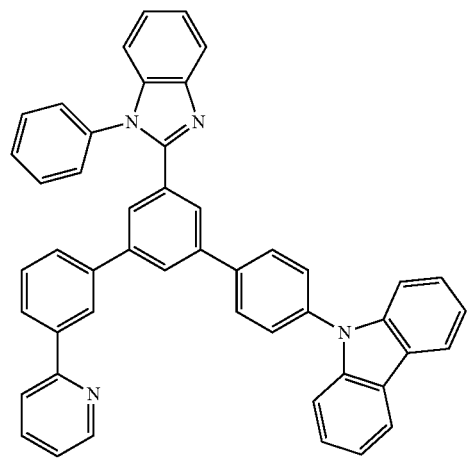
Chemical Formula 51
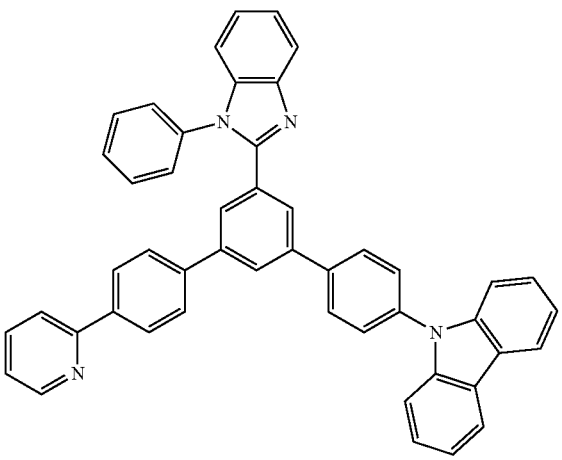
Chemical Formula 52
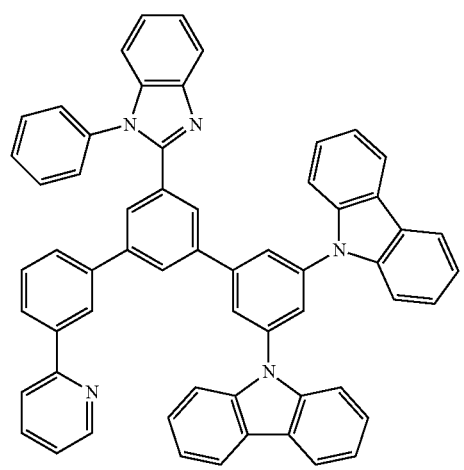
Chemical Formula 53
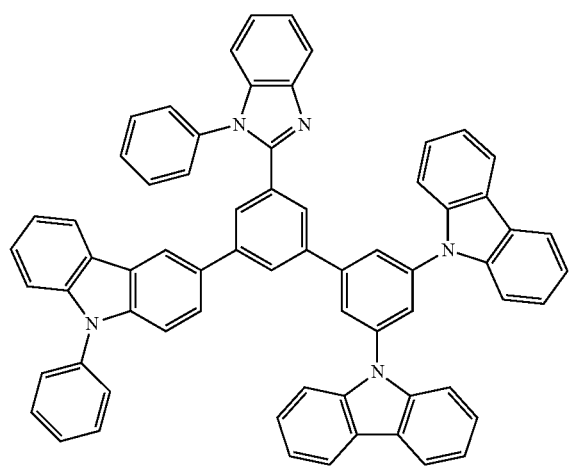
Chemical Formula 54
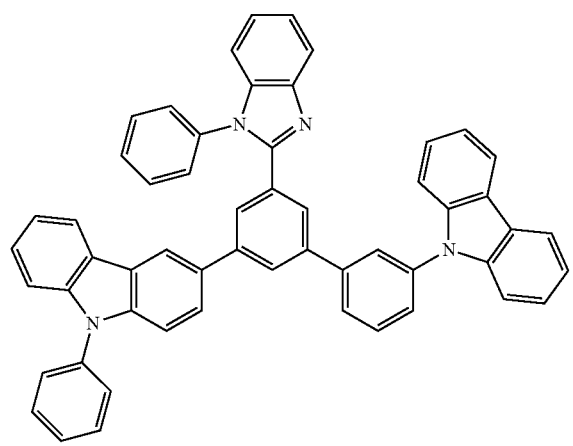
Chemical Formula 55
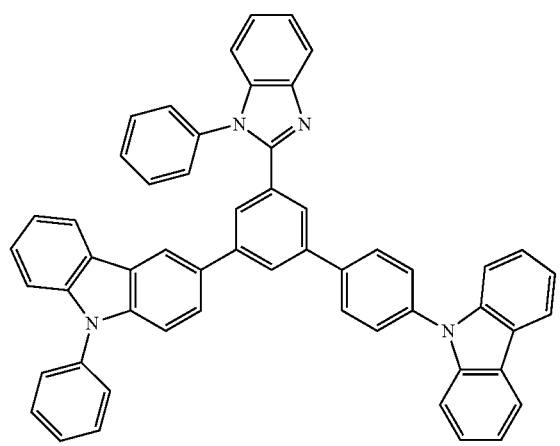

-continued
Chemical Formula 56
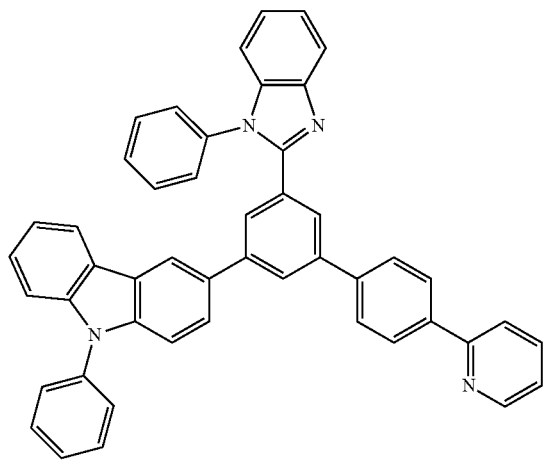
Chemical Formula 57
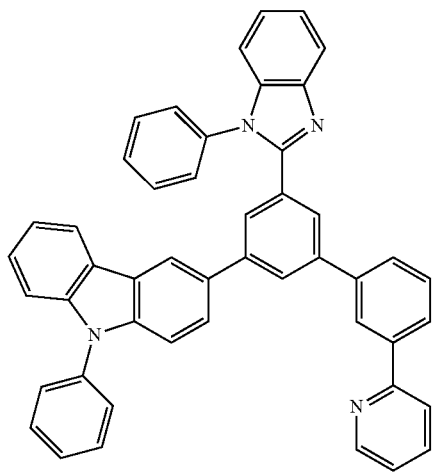
Chemical Formula 58
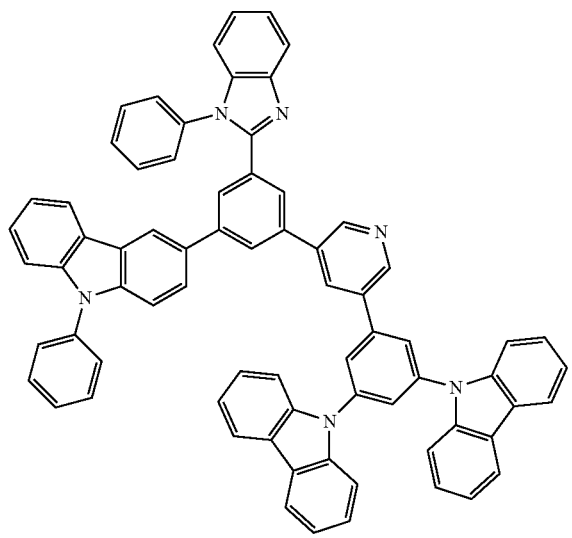
Chemical Formula 59
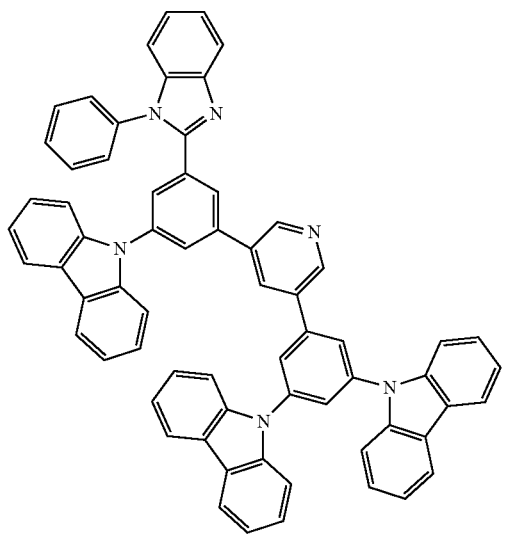
Chemical Formula 60
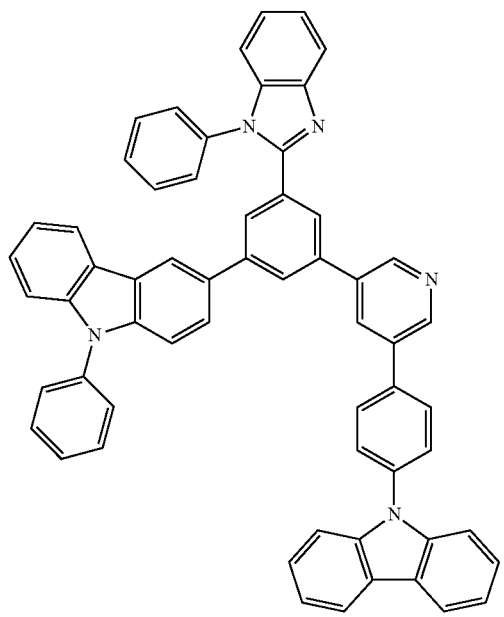
Chemical Formula 61
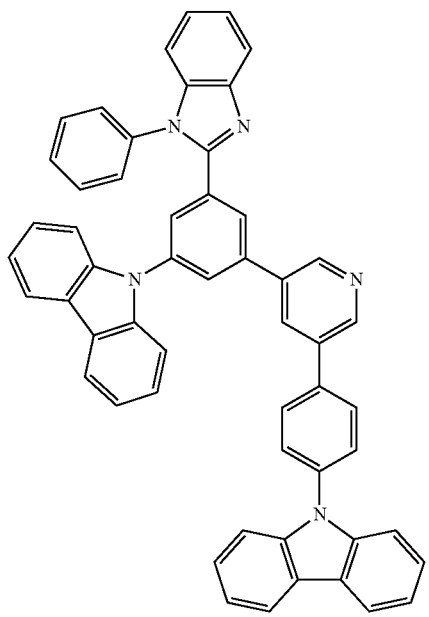

-continued
Chemical Formula 62
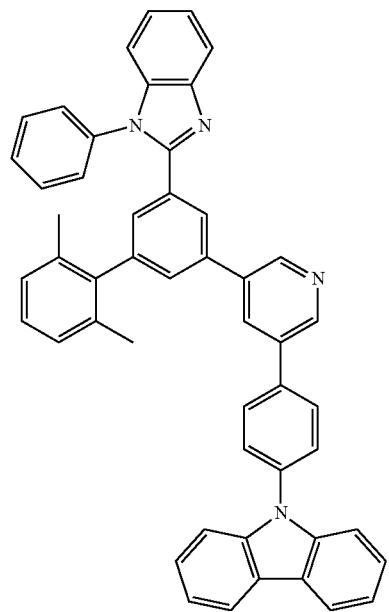
Chemical Formula 63
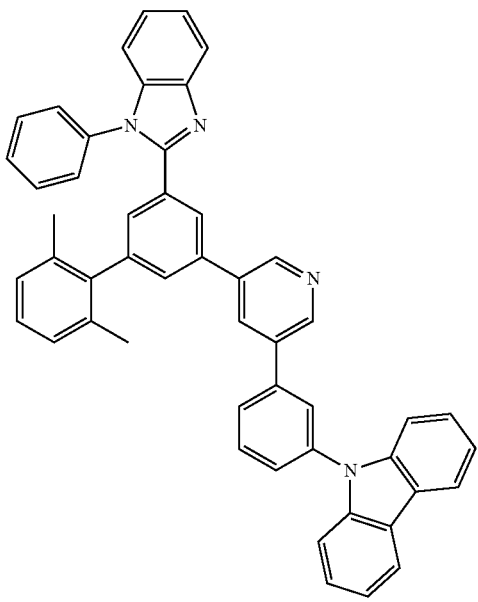
Chemical Formula 64
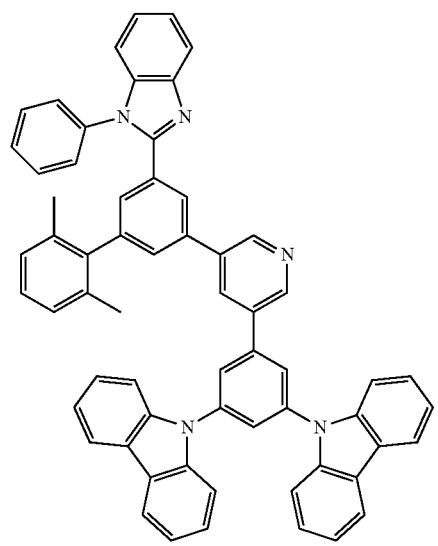
Chemical Formula 65
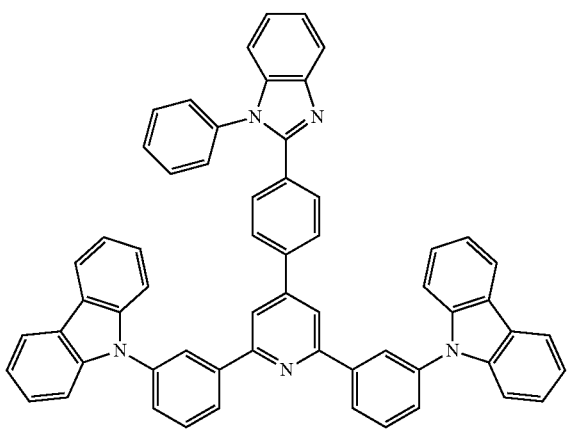

-continued
Chemical Formul 66
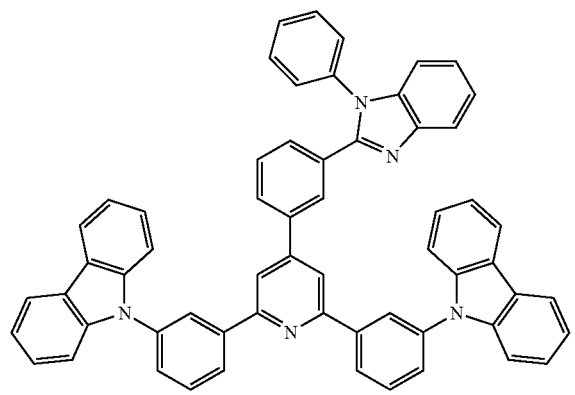
Chemical Formul 67
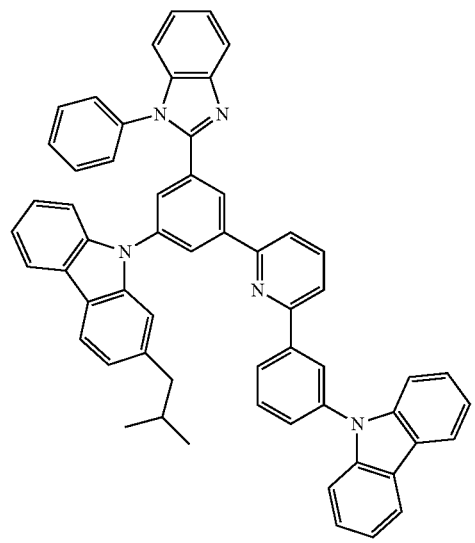
Chemical Formula 68
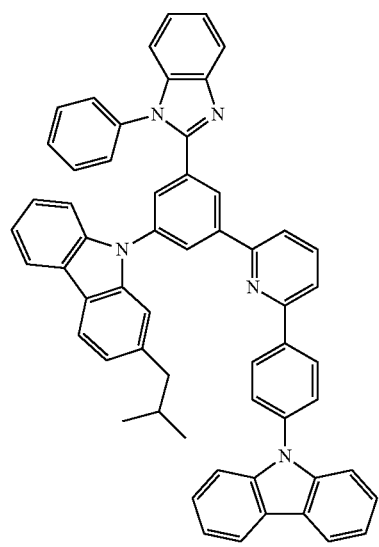
Chemical Formula 69
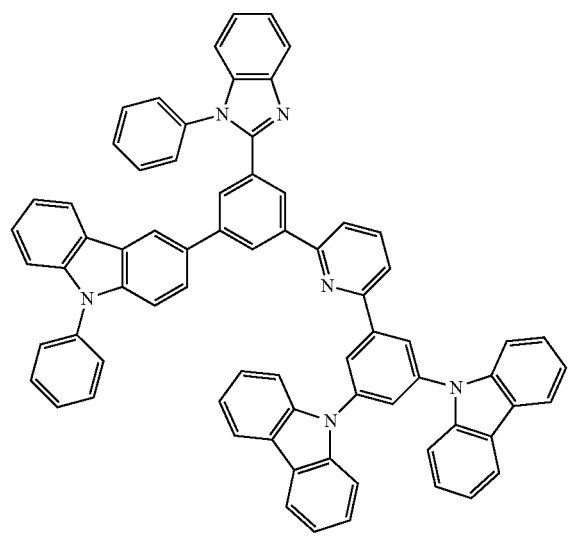

-continued
Chemical Formula 70
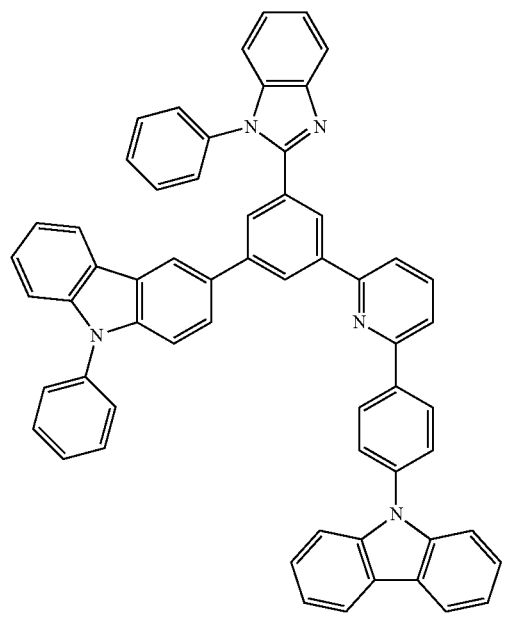
Chemical Formula 71
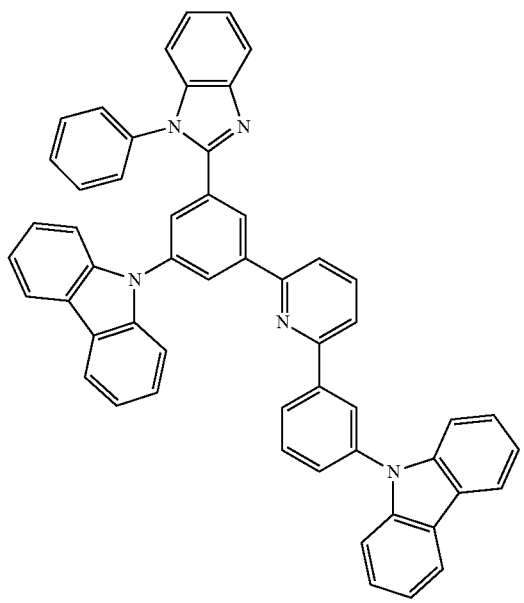
Chemical Formula 72
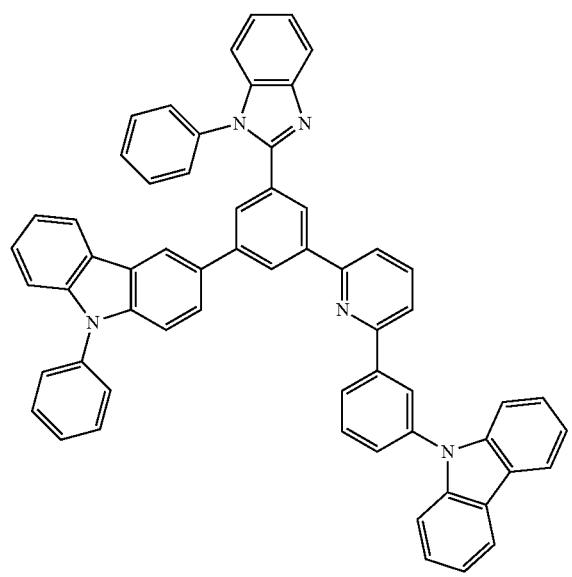
Chemical Formula 73
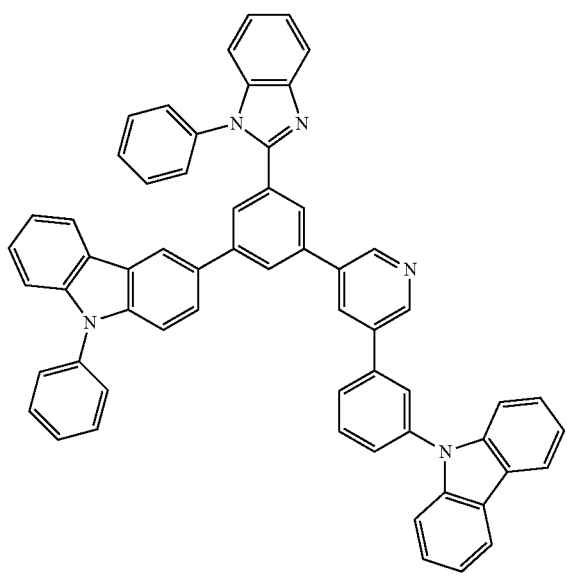

-continued
Chemical Formula 74
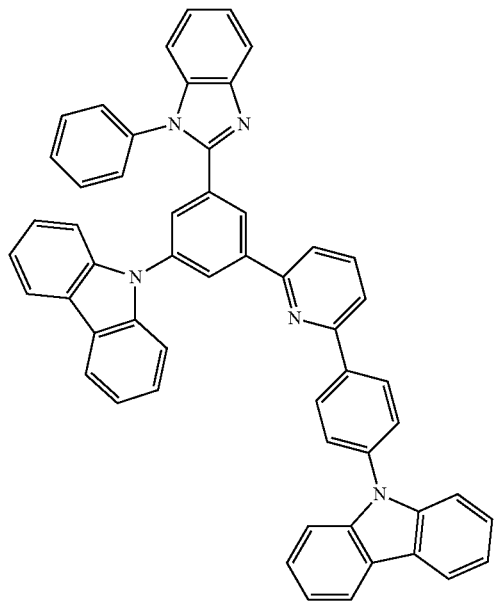
Chemical Formula 75
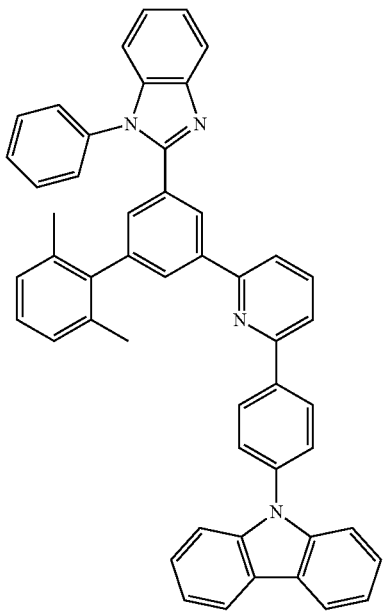
Chemical Formula 76
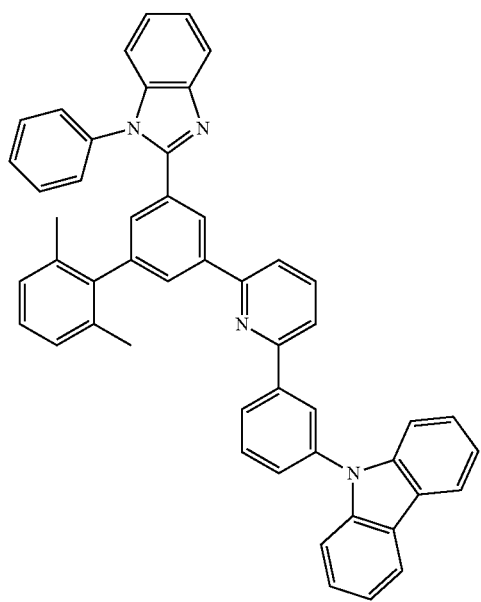
Chemical Formula 77
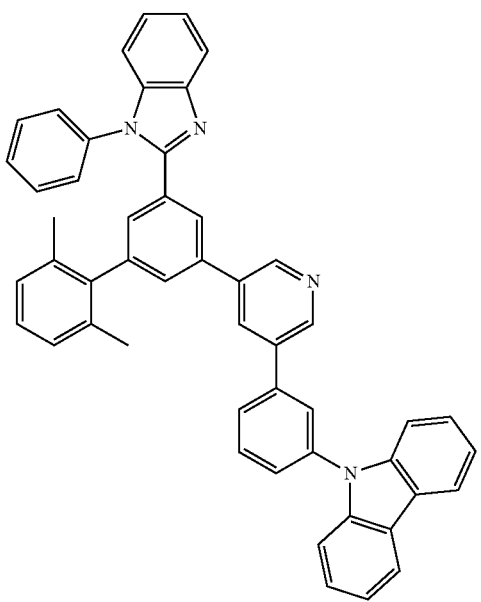

-continued
Chemical Formula 78
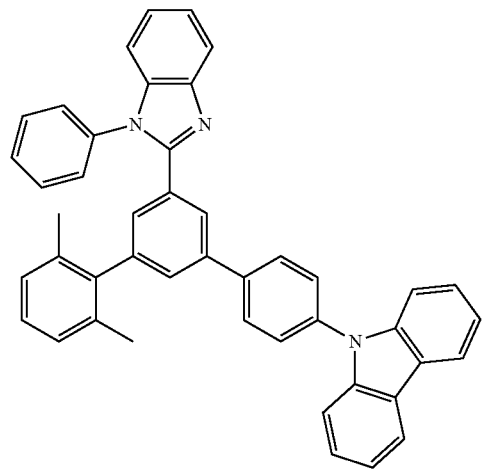
Chemical Formula 79
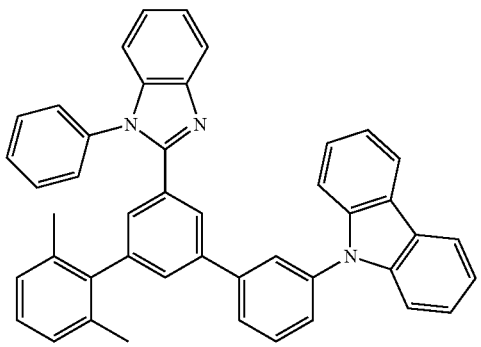
Chemical Formula 80
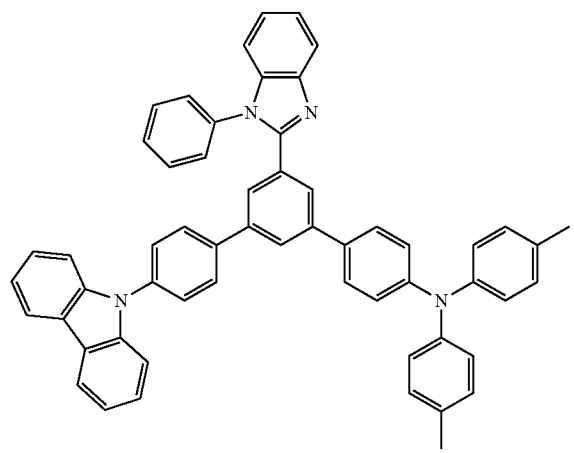
Chemical Formula 81
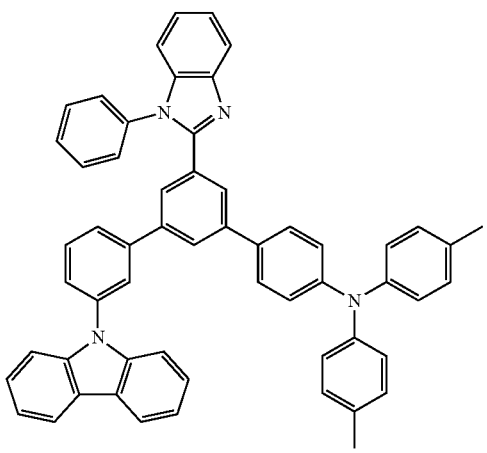
Chemical Formula 82
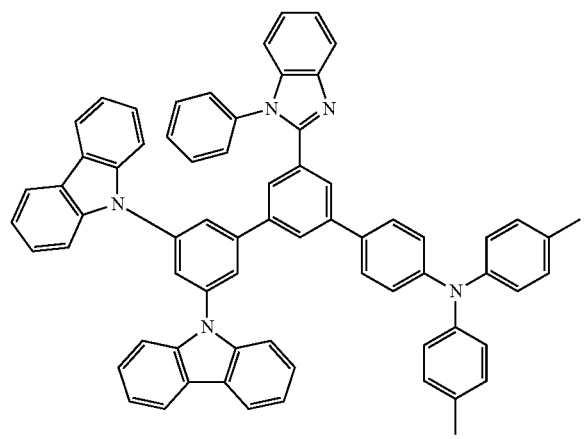
Chemical Formula 83
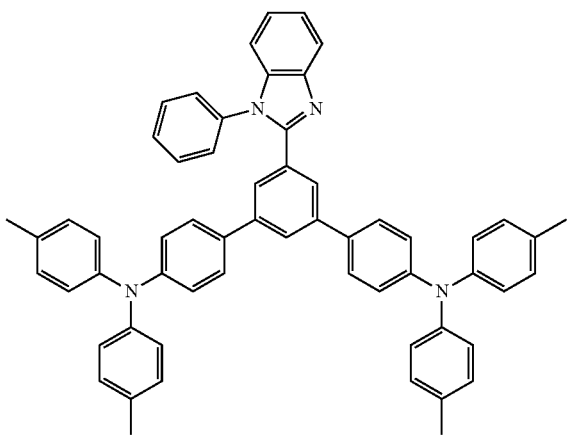

-continued
Chemical Formula 84
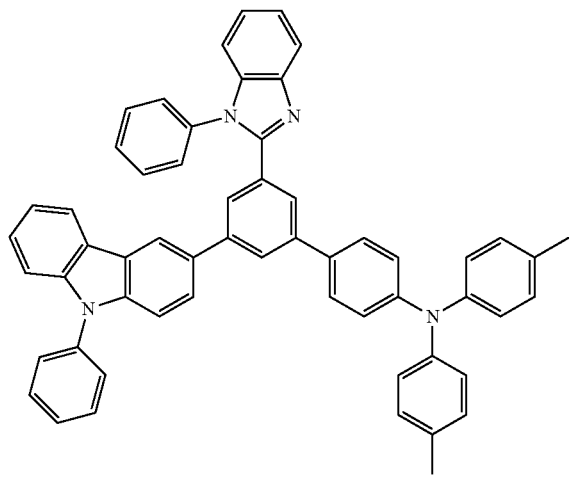
Chemical Formula 85
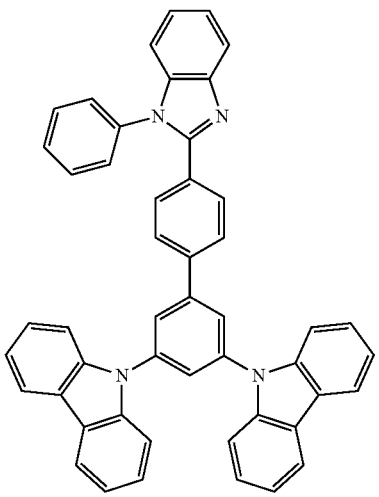
Chemical Formula 86
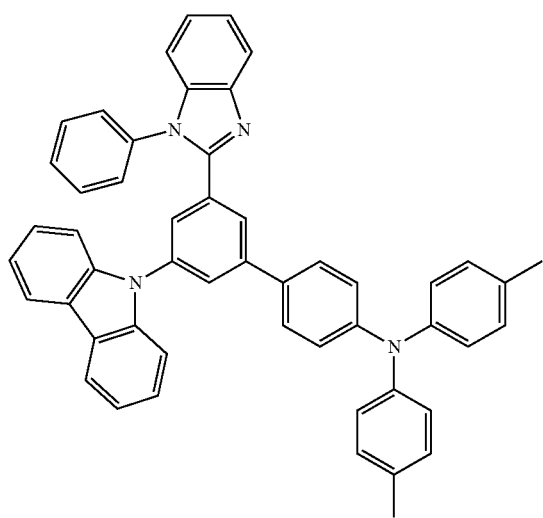
Chemical Formula 87
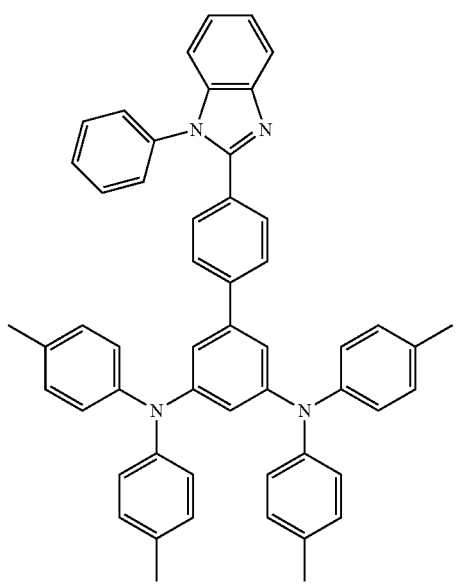

Chemical Formula 88
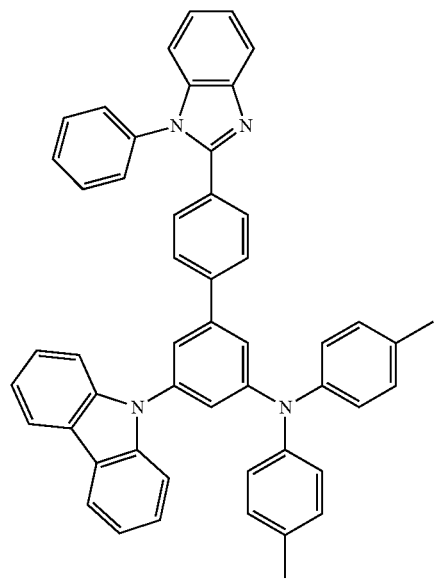
Chemical Formula 89
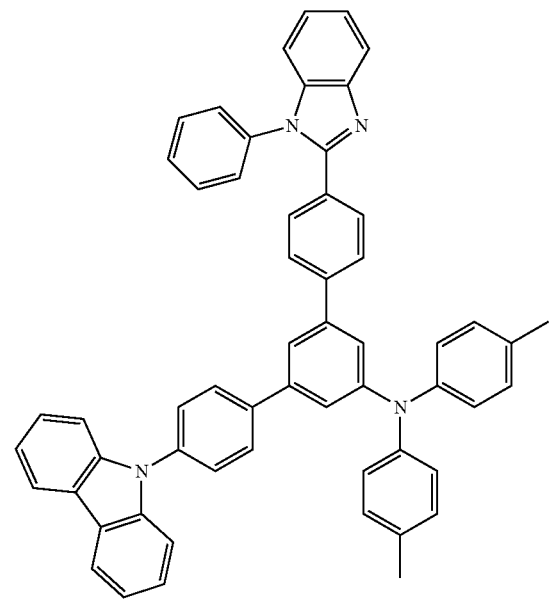
Chemical Formula 90
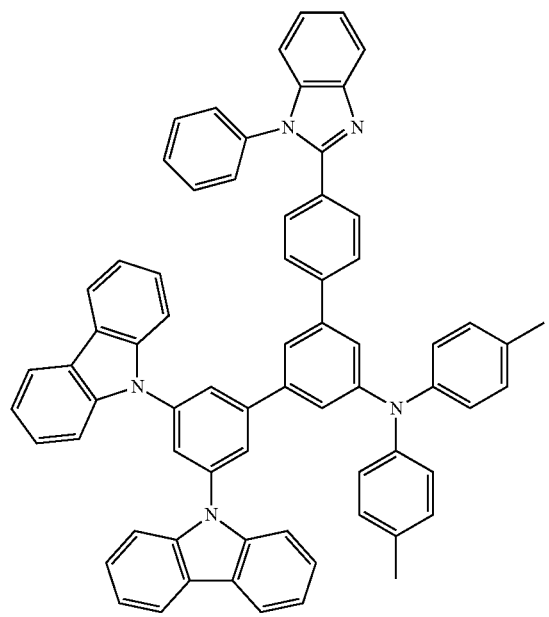
Chemical Formula 91
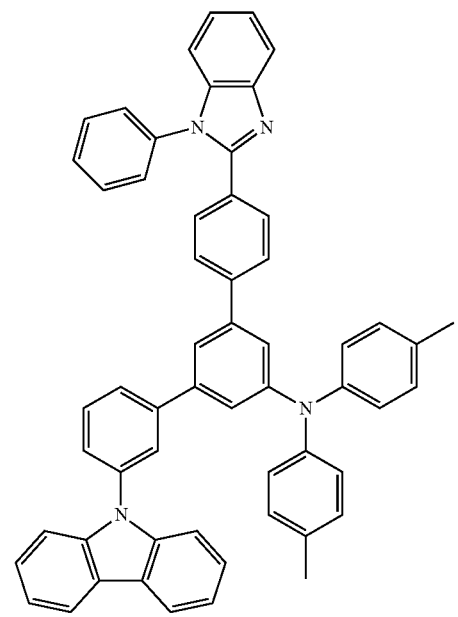

-continued
Chemical Formula 92
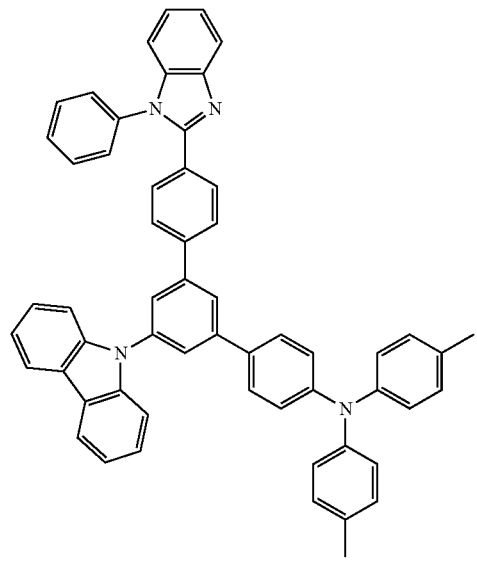
Chemical Formula 93
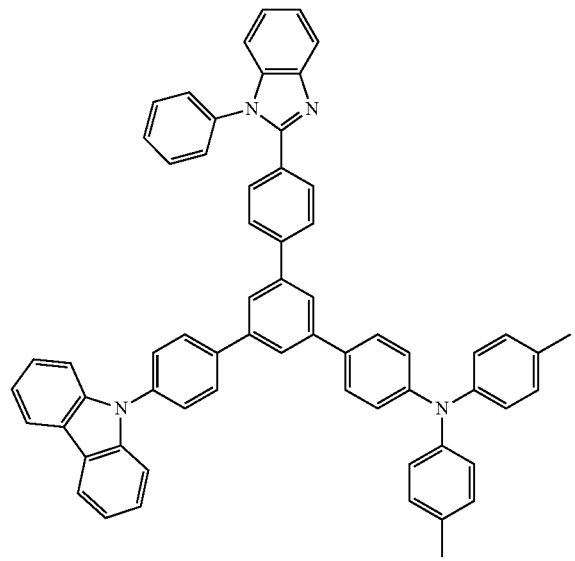
Chemical Formula 94
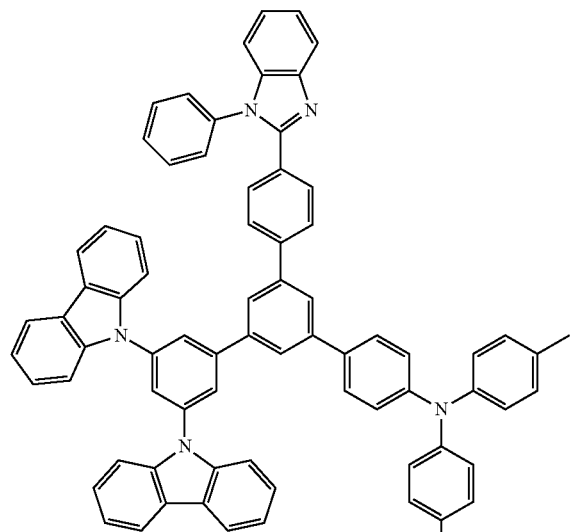
Chemical Formula 95
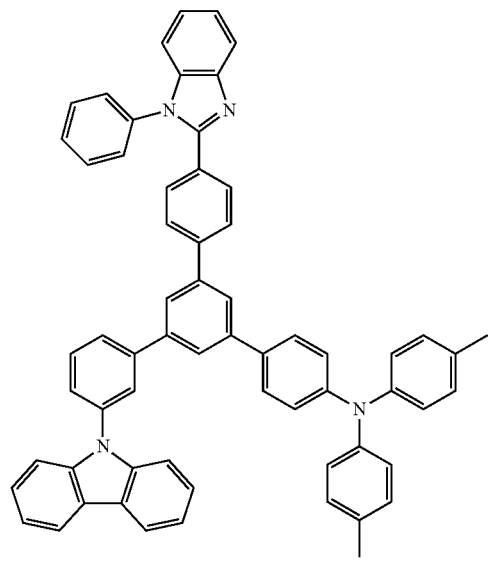
Chemical Formula 96
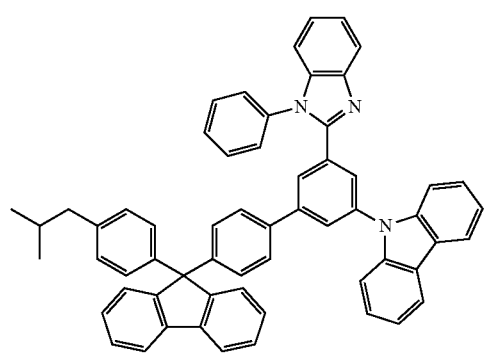
Chemical Formula 97
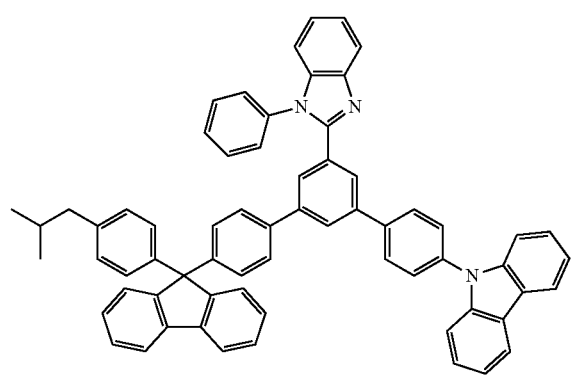

Chemical Formula 98
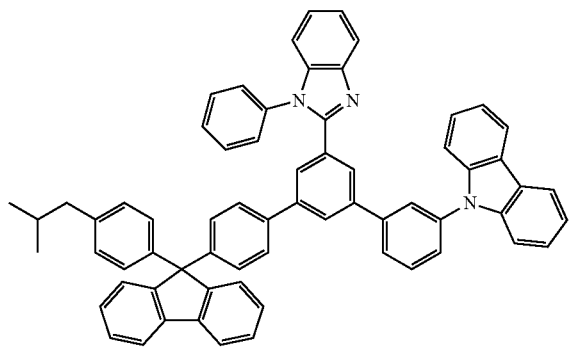
Chemical Formula 99
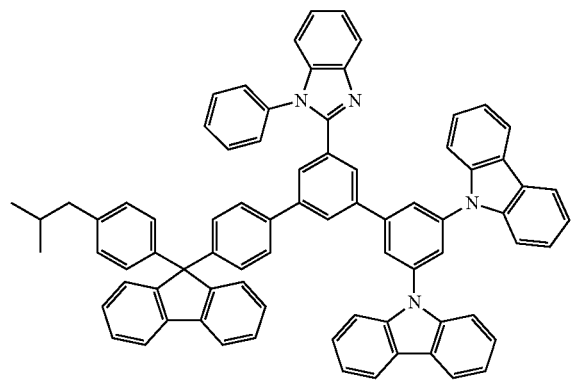
Chemical Formula 100
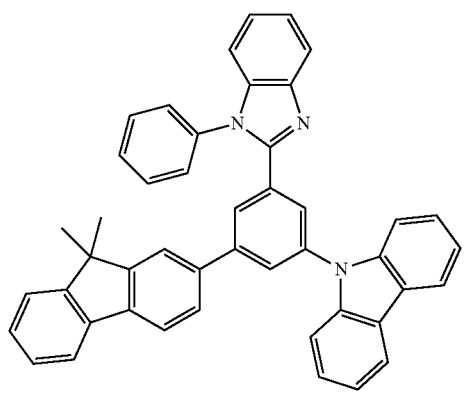
Chemical Formula 101
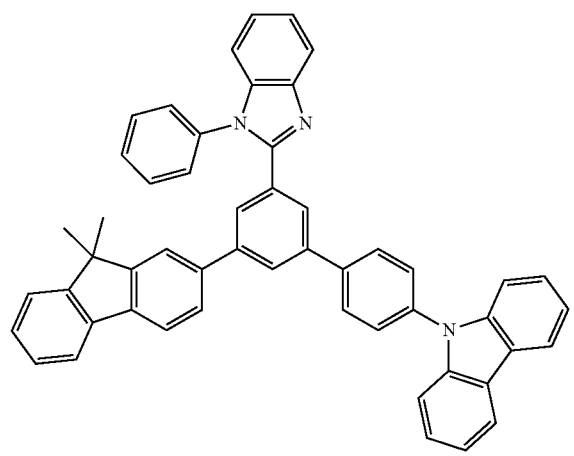
Chemical Formula 102
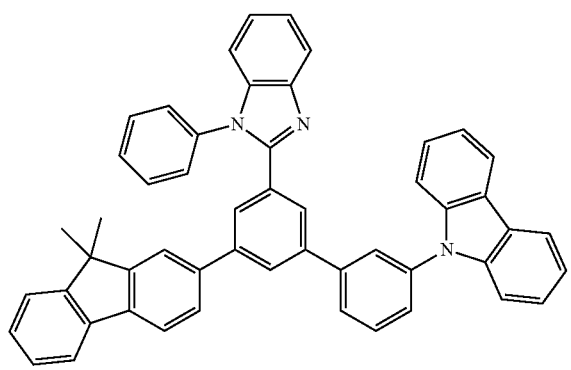
Chemical Formula 103
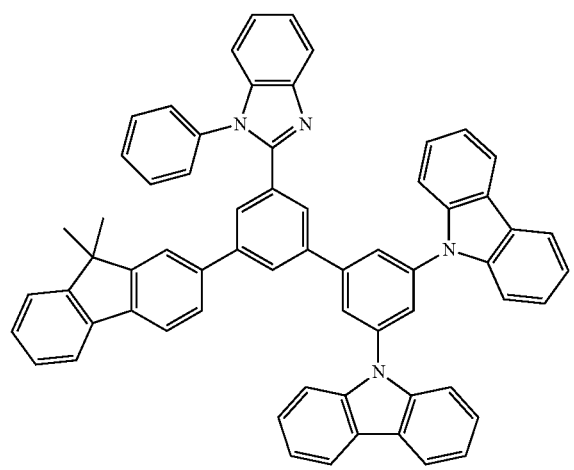

-continued
Chemical Formula 104
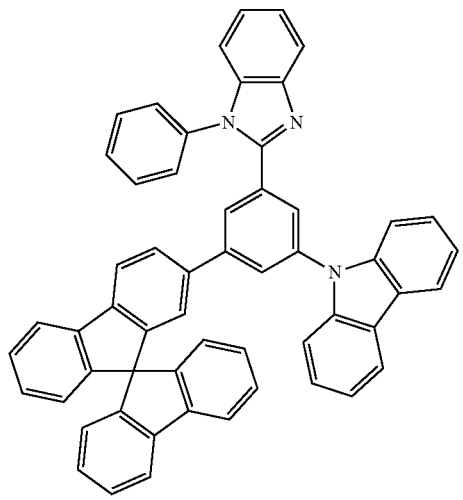
Chemical Formula 105
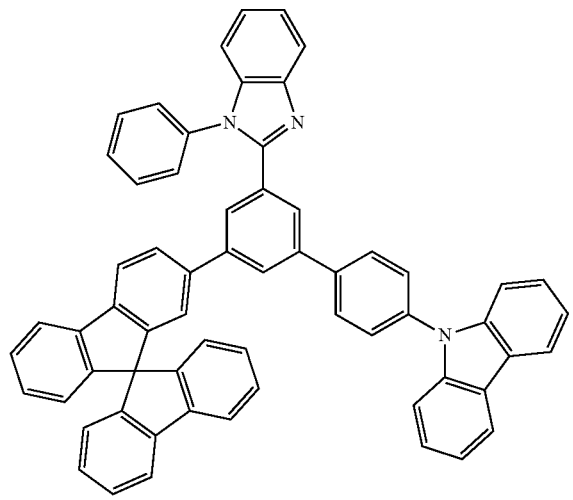
Chemical Formul 106
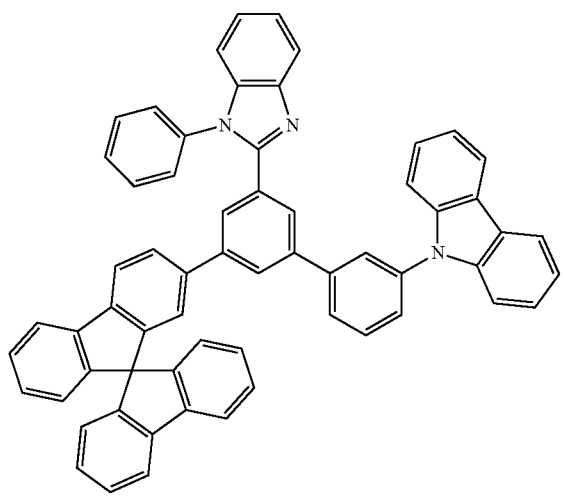
Chemical Formul 107
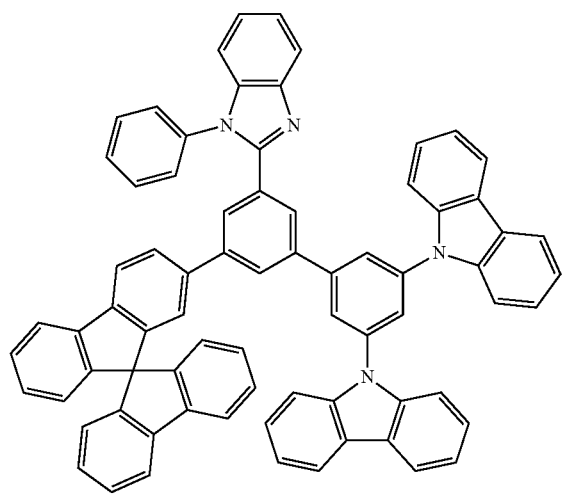
Chemical Formula 108
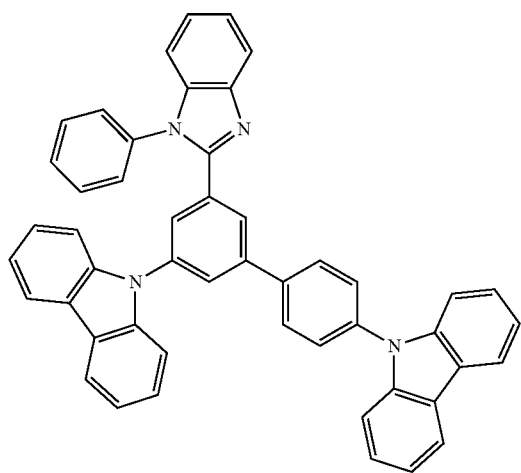
Chemical Formula 109
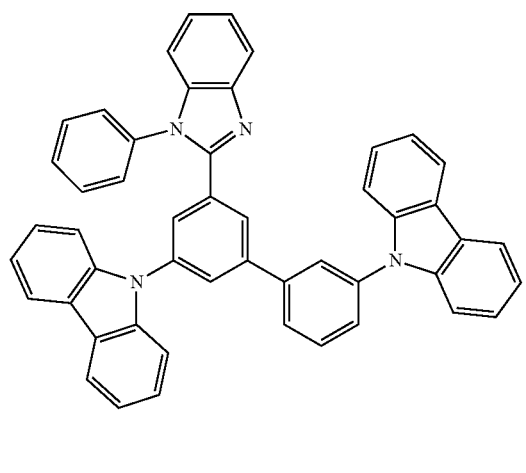

-continued
Chemical Formula 110
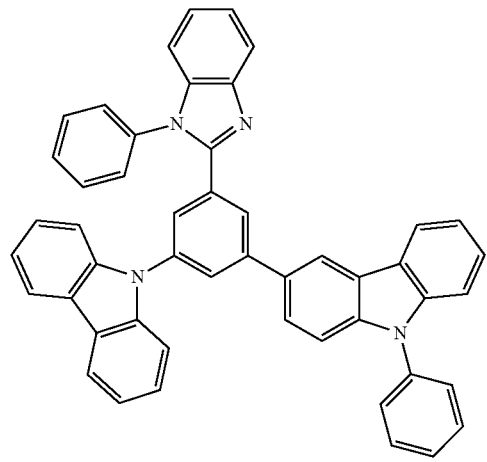
Chemical Formula 111
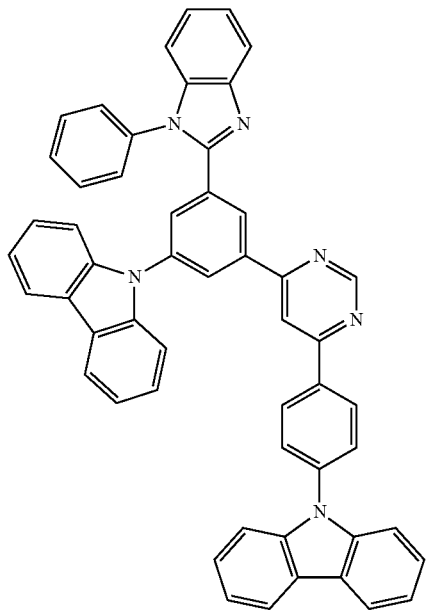
Chemical Formula 112
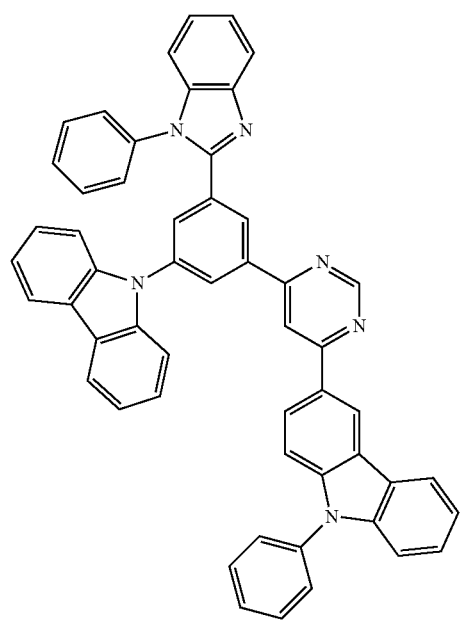
Chemical Formula 113
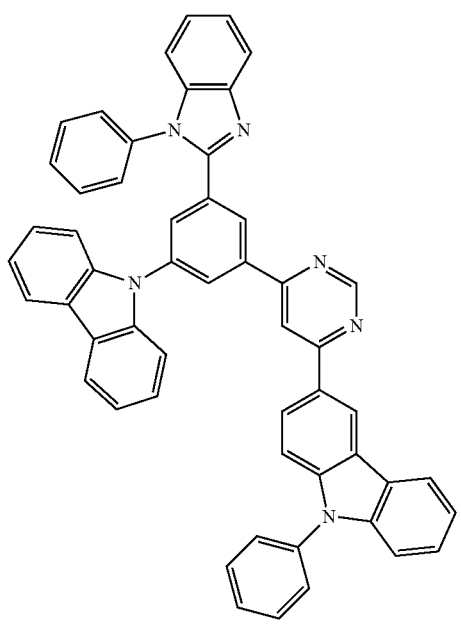

-continued
Chemical Formula 114
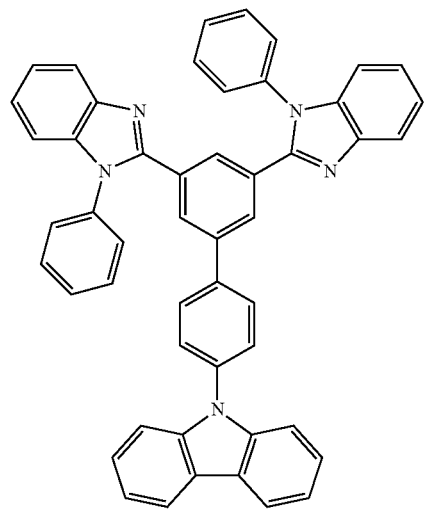
Chemical Formula 115
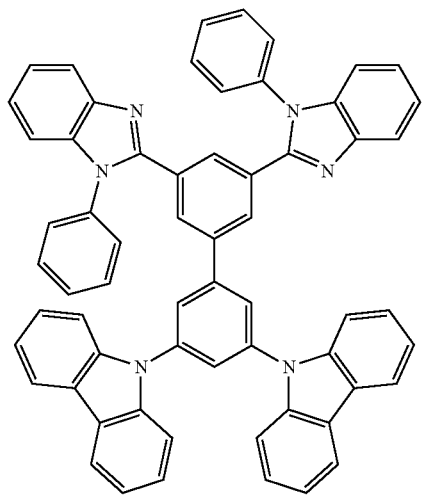
Chemical Formula 116
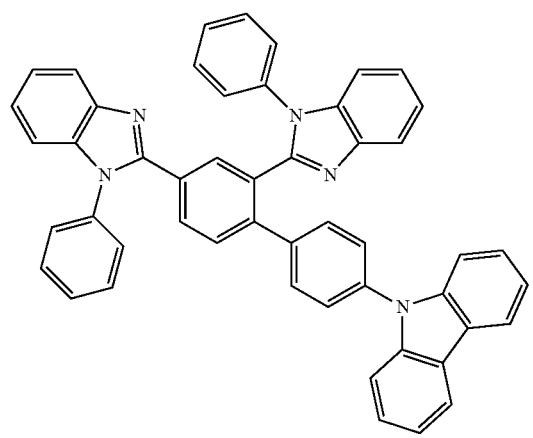
Chemical Formula 117
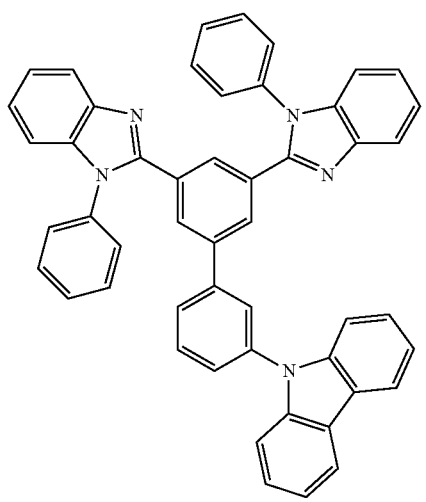
Chemical Formula 118
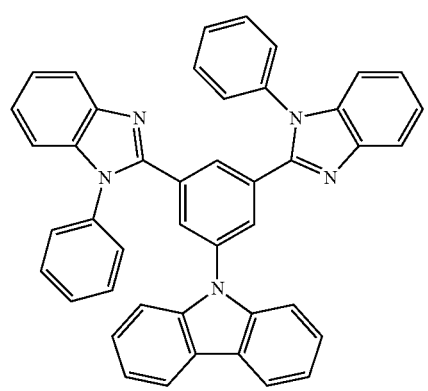
Chemical Formula 119
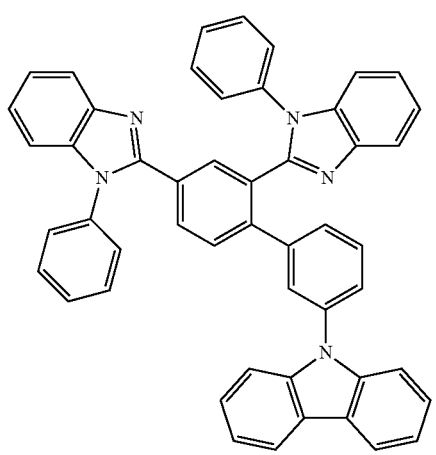

-continued
Chemical Formula 120
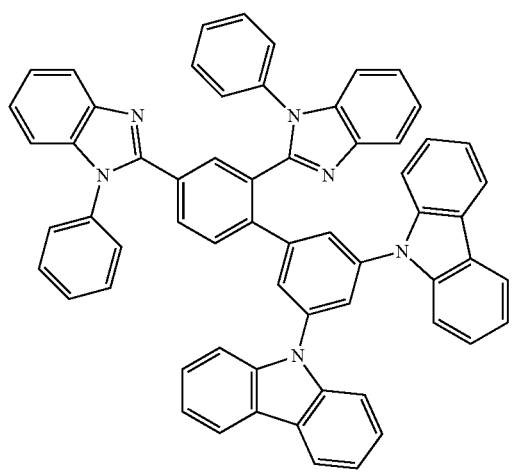
Chemical Formula 121
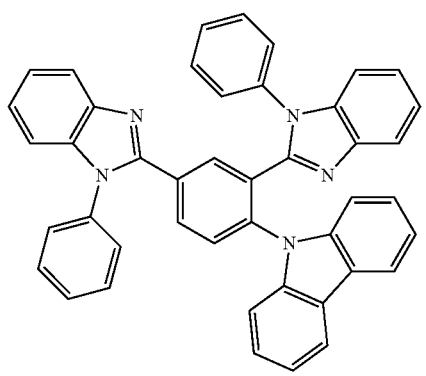
Chemical Formula 122
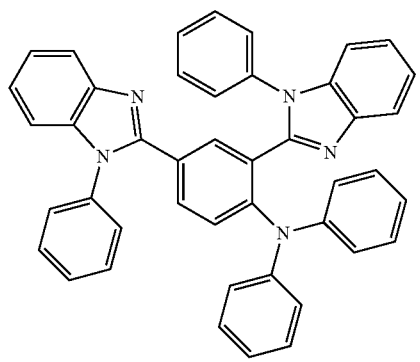
Chemical Formula 123
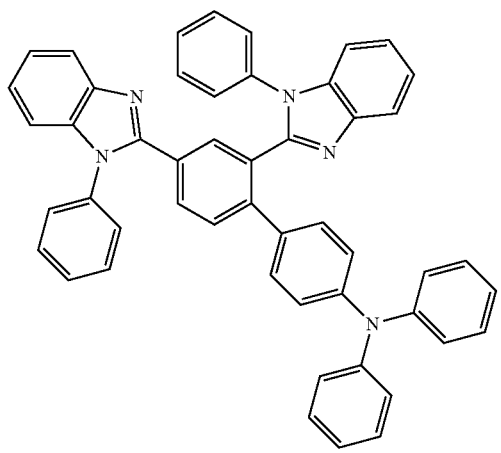
Chemical Formula 124
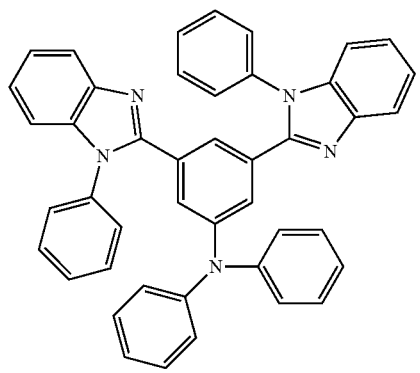
Chemical Formula 125
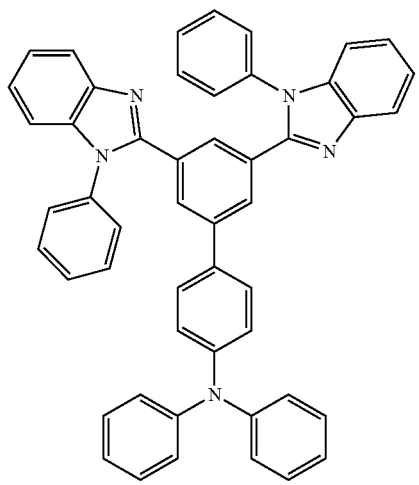

Chemical Formula 126
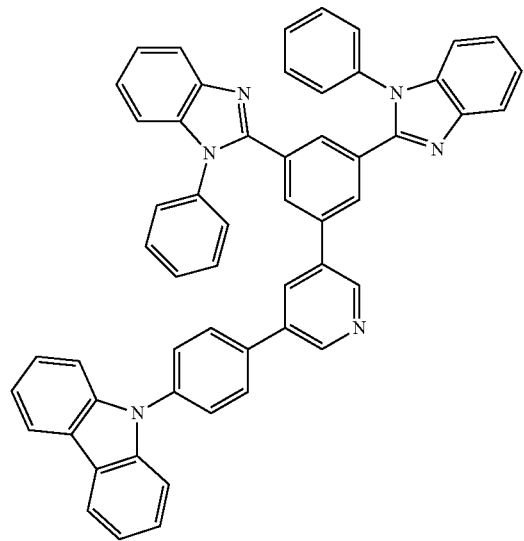
Chemical Formula 127
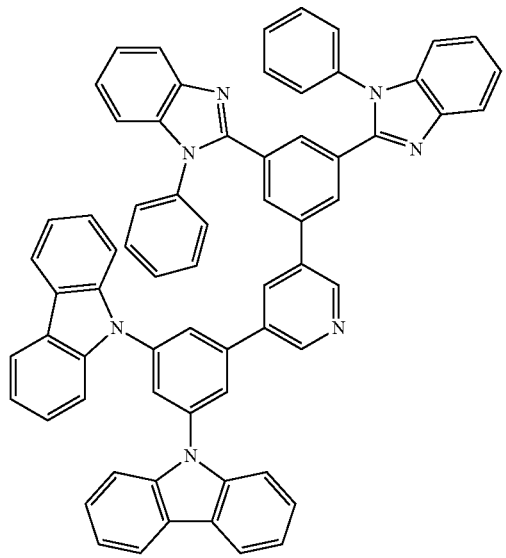
Chemical Formula 128
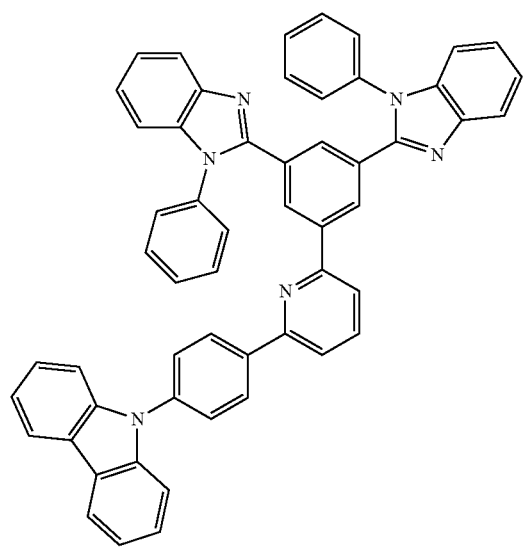
Chemical Formula 129
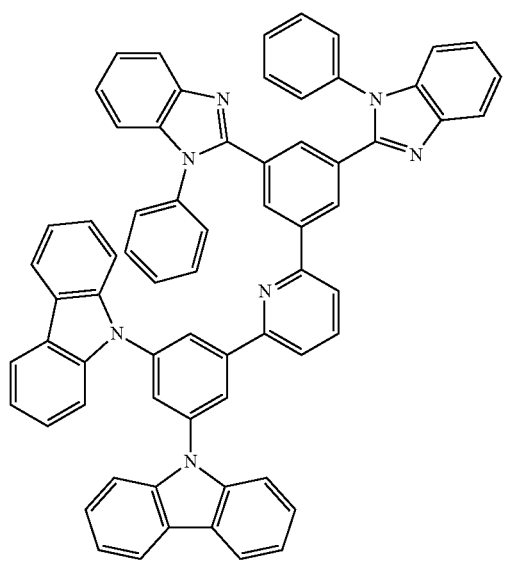

Chemical Formula 130

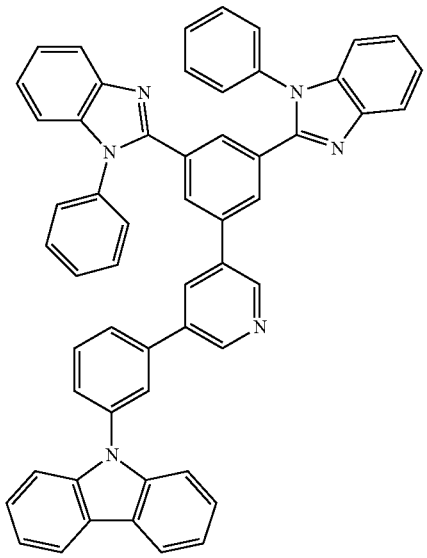

Chemical Formula 131

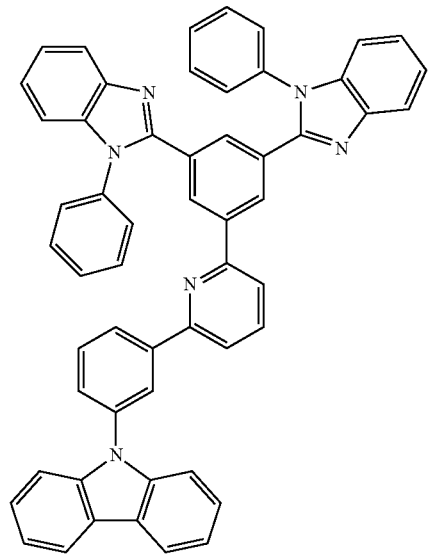

The benzimidazole compound according to an embodiment may be applicable as a host material or a charge transporting material for an organic photoelectric device. The benzimidazole compound may be also used as a non-linear optical material, an electrode material, a chromic material, and/or as materials applicable to an optical switch, a sensor, a module, a waveguide, an organic transistor, a laser, an optical absorber, a dielectric material, and a membrane due to its optical and electrical properties.

When the benzimidazole compound is used in a hole blocking layer or an electron transport layer (ETL) of a light emitting diode, hole blocking properties thereof may be reduced due to the presence of a hole transport backbone. Therefore, when the compound is applied to a hole blocking layer, it is preferable that it does not include a hole transport backbone. Such a hole transport backbone may include, e.g., carbazoles, arylamines, penoxazines, and the like. However, when it is desired that the compound exhibit electron transport and hole transport properties, including the hole transport backbone may improve life-span and reduce a driving voltage of a light emitting diode.

An organic photoelectric device according to an embodiment may include an anode, a cathode, and at least one organic thin layer interposed between the anode and cathode, the at least one organic thin layer including the benzimidazole compound. The organic photoelectric device may be implemented as a display element or device including, e.g., an organic light emitting diode, an organic solar cell, an organic transistor, an organic photo-conductor drum, an organic memory device, and the like. For example, the organic photoelectric device is preferably an organic light emitting diode.

The benzimidazole compound may be used in an emission layer of an organic thin layer. In an implementation, the benzimidazole compound may also be applied to an organic thin layer selected from the group of an electron injection layer (EIL), an electron transport layer (ETL), a hole blocking layer, and combinations thereof.

The organic thin layer between the anode and cathode may include an emission layer. The organic thin layer may further include, e.g., an inter-layer, a hole transport layer (HTL), and an electron transport layer (ETL). The inter-layer may be a buffer layer, e.g., a hole injection layer (HIL), a hole blocking layer, an electron injection layer (EIL), or an electron blocking layer.

FIG. 1 illustrates a schematic cross-sectional view of an organic photoelectric device according to an embodiment. FIG. 1 shows an organic photoelectric device including a substrate 11, an anode 12, a hole transport layer (HTL) 13, an emission layer 14, an electron transport layer (ETL) 15, and a cathode 16.

Referring to FIG. 1, the organic photoelectric device may be fabricated using the benzimidazole compound of an embodiment as follows.

First, an anode 12 material may be coated on an upper side of the substrate 11.

The substrate 11 may be a glass substrate or a transparent plastic substrate having excellent transparency, face smoothness, handling ease, and water repellency.

The anode 12 may include a transparent and highly conductive material, e.g., indium tin oxide (ITO), tin oxide ($SnO_2$), zinc oxide (ZnO), and the like.

Then, the hole transport layer (HTL) 13 may be disposed on the anode 12 using, e.g., vacuum deposition, sputtering, or spin coating. Then, the emission layer 14 may be disposed on the hole transport layer (HTL) 13 using, e.g., vacuum deposition or a solution coating method such as spin coating, inkjet printing, and the like.

The electron transport layer (ETL) 15 may be disposed between the emission layer 14 and the cathode 16.

The emission layer 14, the hole transport layer (HTL) 13, and the electron transport layer (ETL) 15 may have a predetermined thickness, but are not specifically limited. For example, the emission layer 14 may have a thickness of about 5 nm to about 1 μm, and preferably about 10 to about 500 nm. In an implementation, the hole transport layer (HTL) 13 and electron transport layer (ETL) 15 may respectively have a thickness of about 10 to about 10,000 Å.

The electron transport layer (ETL) 15 may be formed using, e.g., vacuum deposition, sputtering, or spin coating of generally-used electron transport layer (ETL) 15 materials.

The hole transport layer (HTL) 13 and the electron transport layer (ETL) 15 may efficiently transport a carrier to the emission layer 14 to facilitate light emitting recombination in the emission layer 14.

The hole transport layer (HTL) 13 material may include, but is not limited to, poly(3,4-ethylenedioxy-thiophene) (PEDOT) doped with poly(styrenesulfonic acid) (PSS), and N,N'-bis(3-methylphenyl)-N,N-diphenyl-[1,1'-biphenyl]-4,4'-diamine (TPD).

The electron transport layer (ETL) 15 material may include, but is not limited to, aluminum trihydroxyquinoline (Alq$_3$), a 1,3,4-oxadiazole derivative such as 2-(4-biphenylyl-5-phenyl-1,3,4-oxadiazole (PBD), a quinoxaline derivative such as 1,3,4-tris[(3-phenyl-6-trifluoromethyl)quinoxalin-2-yl]benzene (TPQ), and a triazole derivative.

The emission layer 14 may include the benzimidazole compound of an embodiment. The benzimidazole compound of an embodiment may be mixed with a phosphorescent light-emitting organic compound. For example, the benzimidazole compound of an embodiment may be a host doped with the phosphorescent light-emitting organic compound. The phosphorescent organic compound may be a phosphorescent light emitting organic metal complex that emits from its triplet state, and is preferably a metal complex of at least one group VIII metal ion according to the periodic table of Gregor Johann Mendel. The group VIII metal ion may include one of, e.g., Fe, Co, Ni, Ru, Rh, Pd, Os, Ir, and Pt, and is preferably Ir or Pt.

Examples of the metal complex may be represented by the following Chemical Formulae 132 to 134, but are not limited thereto.

Chemical Formula 132

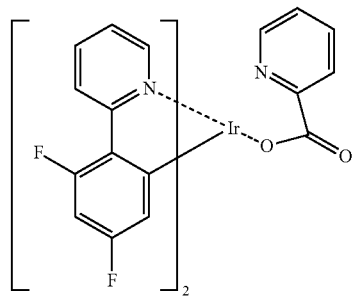

Chemical Formula 133

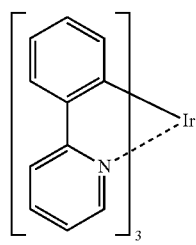

Chemical Formula 134

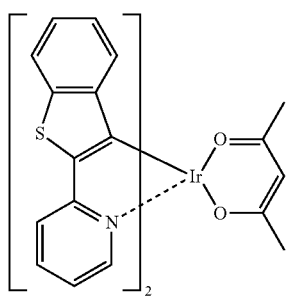

When the organic layer including the organic compound is formed using a solution coating, another low molecular weight host material may be included along with the organic compound. Examples of the low molecular weight host material may include compounds represented by the following Chemical Formulae 135 to 138, but are not limited thereto.

Chemical Formula 135

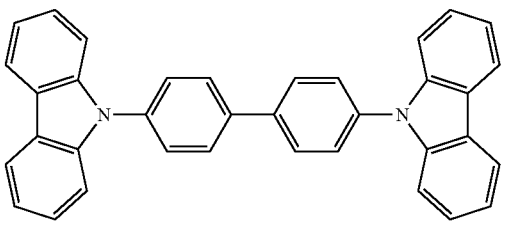

Chemical Formula 136

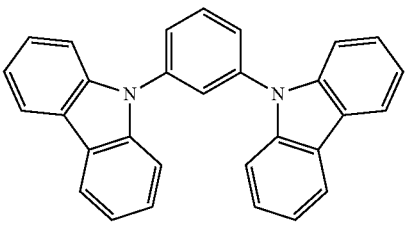

Chemical Formula 137

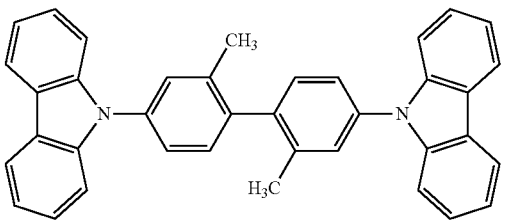

Chemical Formula 138

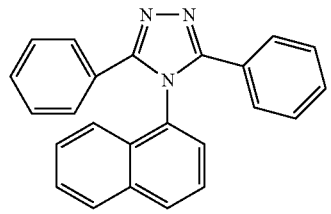

The benzimidazole compound may be used by mixing with polymers having conjugated double bonds, e.g., fluorene-based polymers, polyphenylenevinylene-based polymers, and/or polyparaphenylene-based polymers, and also by mixing with binder resins.

The binder resins may include, e.g., polyvinylcarbazole (PVK), polycarbonate, polyester, polyan arylate, polystyrene, acryl polymers, methacryl polymers, polybutyral, polyvinylacetal, diallylphthalate polymers, phenol resins, epoxy resins, silicone resins, polysulfone resins, and/or urea resins. These resins can be used singularly or in combinations thereof.

Selectively, a hole blocking layer may be disposed using vacuum deposition to limit transport speed of holes into the emission layer 14 and thus to increase the recombination opportunity of electrons and holes.

A cathode 16 material may be coated on the electron transport layer (ETL).

The cathode material may include, e.g., lithium (Li), magnesium (Mg), calcium (Ca), aluminum (Al), Al:Li, Ba:Li, or Ca:Li having a small work function.

EXAMPLES

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

In the following Examples 1 to 6, compounds M-1 to M-9 for preparing a benzimidazole compound according to an embodiment were respectively prepared as shown in Reaction Schemes 1 to 9.

Synthesis Example 1

Synthesis of Compound M-1

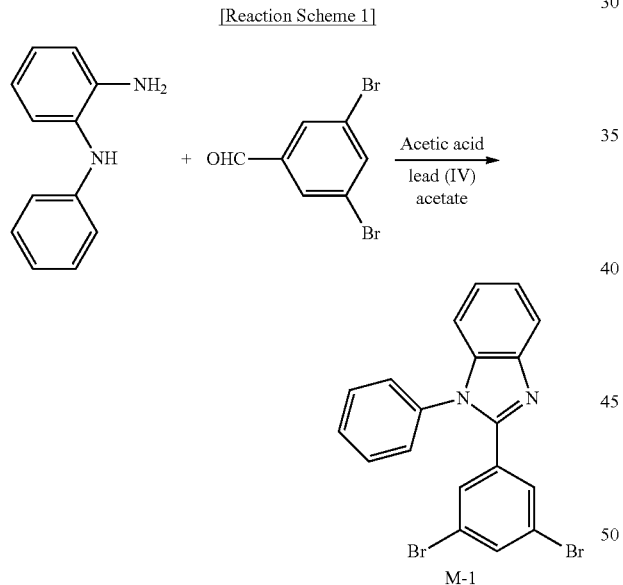

[Reaction Scheme 1]

50 g (189 mmol) of 3,5-dibromobenzaldehyde and 38.3 g (208 mmol) of N-phenyl-o-phenylenediamine were put in a 500 mL round bottom flask, and 200 mL of acetic acid was added thereto. The resulting mixture was agitated for 30 minutes at room temperature; and 100 g (227 mmol) of lead (IV) acetate was added thereto. The resulting product was agitated for 12 hours at room temperature. When the reaction was complete, the acetic acid was removed under reduced pressure. The reactant was dissolved in methylene chloride and washed five times with water. The organic solution was dried with anhydrous magnesium sulfate to remove the solvent. Then, the acquired solid was purified with a silica gel column in a methylene chloride solvent. The resulting product was recrystallized in a mixed solvent of methylene chloride/hexane in a ratio of 1:6, providing 34 g of a solid indicated as compound M-1 in the reaction scheme 1 (yield: 42%).

Example 1

Synthesis of Compound M-2

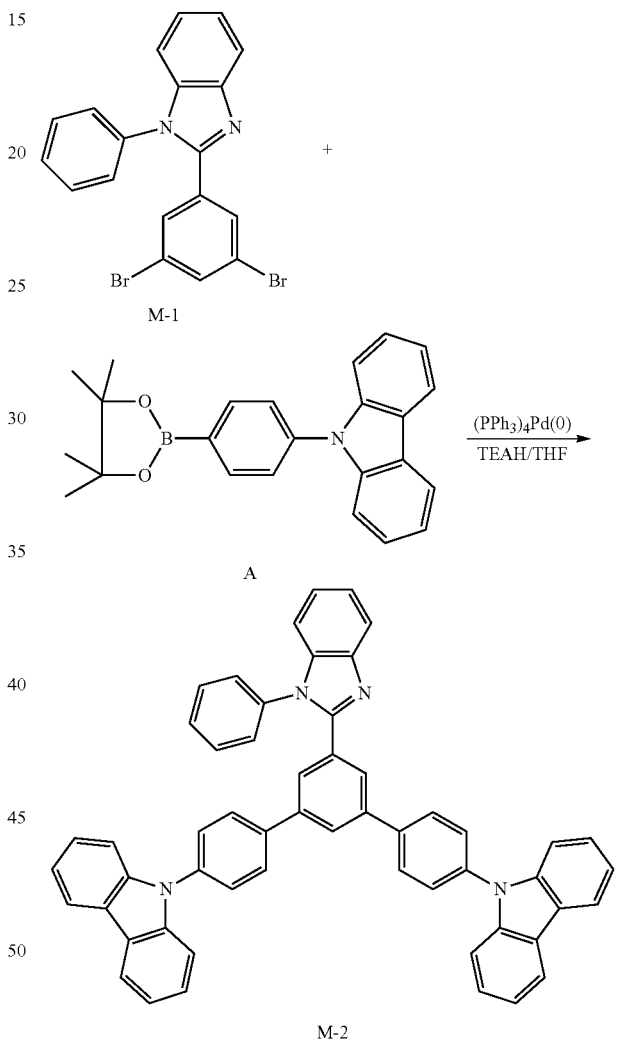

Reaction Scheme 2

1.0 g of compound M-1 (2.3 mmol), 1.89 g of a material A (5.1 mmol), and 0.23 g of tetrakis(triphenylphosphine) palladium (0.19 mmol) were dissolved in 30 mL of tetrahydrofuran (THF) under an argon atmosphere in a 100 mL round bottom flask having a thermometer, a reflux condenser, and an agitator. Then, 15 mL of 20% tetratriethylammonium hydroxide was added thereto. The resulting product was agitated at 75° C. for 24 hours. When the reaction was complete, the reactant was cooled to room temperature and then extracted several times with methylene chloride and washed with water. The washed reactant was treated with anhydrous magnesium sulfate to remove moisture therefrom. The resulting reactant was filtered to remove the solvent. When the solvent was removed, the acquired solid was recrystallized with a mixed solvent of methylene chloride/hexane in a ratio of 1:6, preparing 1.2 g of a white compound M-2 (yield: 68.4%). This was sublimated and purified to prepare 0.79 g of a white crystal. This crystal had a maximum light emitting wavelength at 383 nm when it was fabricated into a thin film. It had an LC-MS theoretical value of $C_{55}H_{36}N_4$ [MH]$^+$753.2940 and a measurement value of 753.2978.

Example 2

Synthesis of Compound M-3

Reaction Scheme 3

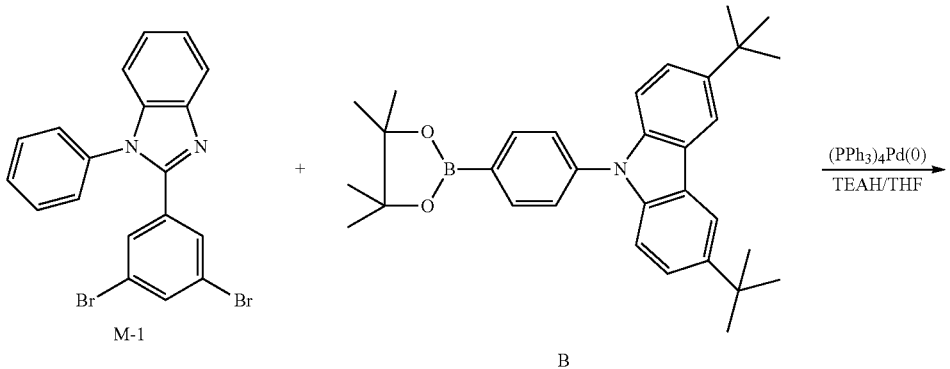

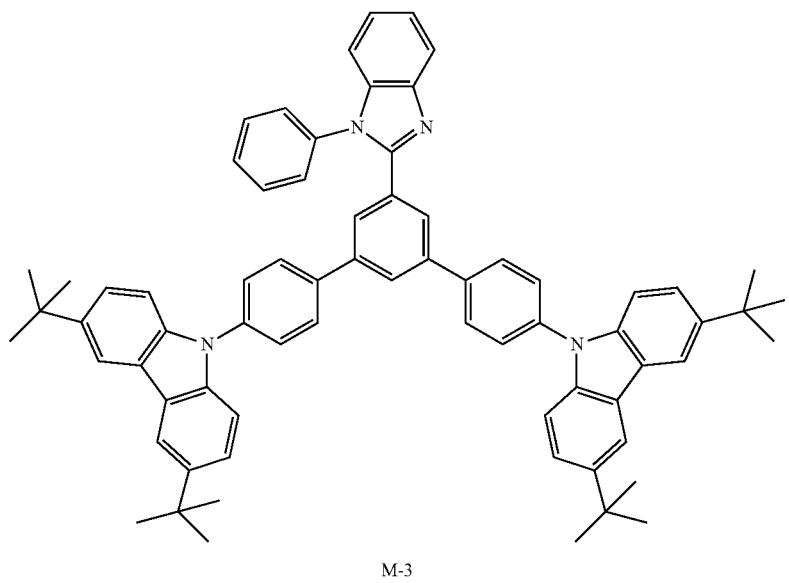

M-3

1.0 g (2.3 mmol) of compound M-1, 2.37 g (4.9 mmol) of a material B, and 0.23 g (0.19 mmol) of tetrakis(triphenylphosphine)palladium were dissolved in 30 mL of THF under an argon atmosphere in a 100 mL round bottom flask having a thermometer, a reflux condenser, and an agitator, and 15 mL of 20% tetratriethylammonium hydroxide was added thereto. The resulting mixture was agitated at 75° C. for 24 hours. When the reaction was complete, the reactant was cooled to room temperature and then extracted several times with methylene chloride and washed with water. Then, the washed reactant was treated with anhydrous magnesium sulfate to remove moisture and filtered to remove the solvent. The resulting product was purified through a silica gel column with a methylene chloride solvent, preparing 1.78 g of a white compound M-3 (yield: 78.1%). When it was fabricated into a thin film, it had a maximum light emitting wavelength at 388 nm. It had an LC-MS theoretical value of $C_{71}H_{68}N_4$ $[MH]^+$ 977.5444 and measurement value of 977.5442.

Example 3

Synthesis of Compound M-4 of N,N-dimethylsulfoxide (DMSO) under an argon atmosphere in a 250 mL round bottom flask having a thermometer, a reflux condenser, and an agitator. The resulting solution was agitated at 150° C. for 48 hours and cooled to room temperature. Then, DMSO was removed therefrom under reduced pressure. The remaining solid was dissolved in methylene chloride. The solution was washed several times with water to remove moisture with anhydrous magnesium sulfate. The resulting product was filtered to remove the solvent. The acquired solid was purified through a silica gel column with a methylene chloride solvent, preparing 5.5 g of a white compound M-4 (yield: 65.4%). When it was prepared into a thin film, it had a maximum light emitting wavelength at 394 nm. It had an LC-MS theoretical value of $C_{43}H_{28}N_4$ $[MH]^+$ 601.2314 and a measurement value of 601.2384.

Synthesis Example 2

Synthesis of Compound M-5

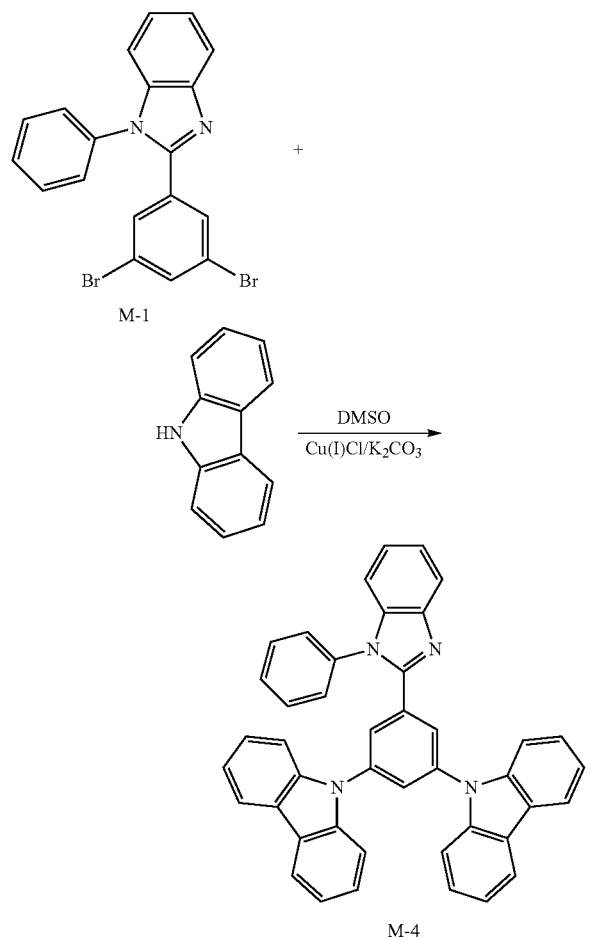

Reaction Scheme 4

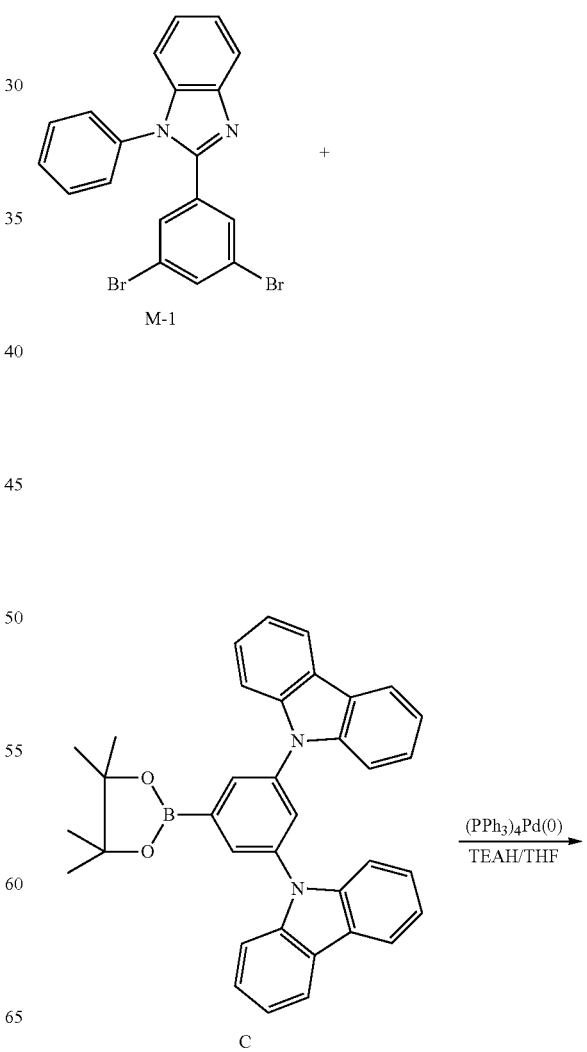

Reaction Scheme 5

6 g (14 mmol) of compound M-1, 5.8 g (35 mmol) of carbazole, 1.5 g (15.1 mmol) of copper (I) chloride, and 6 g (43 mmol) of potassium carbonate were dissolved in 100 mL

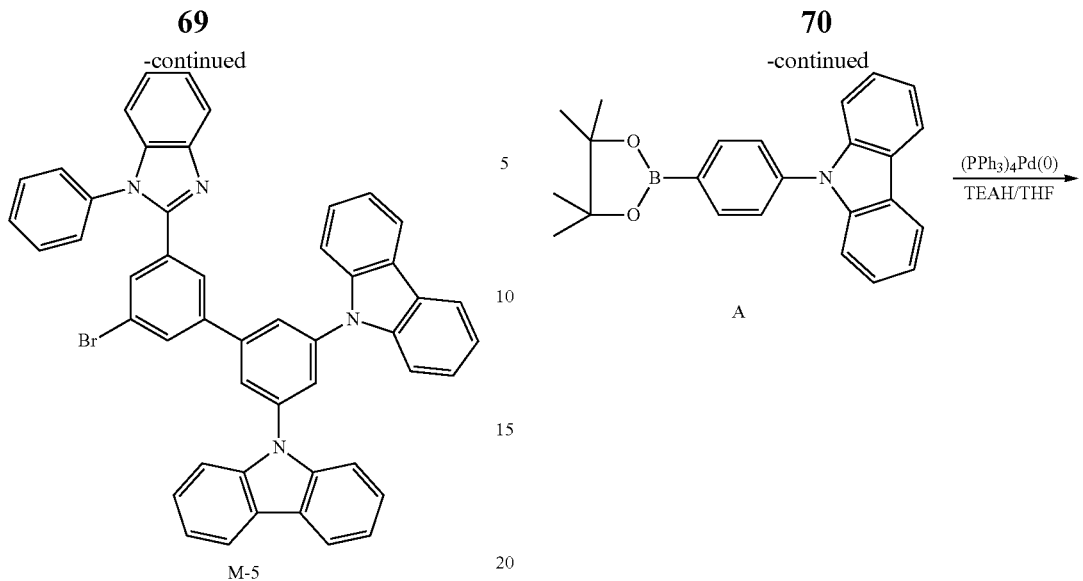

M-5

3.0 g (7.0 mmol) of compound M-1, 3.74 g (7.0 mmol) of a material C, and 0.16 g (0.14 mmol) of tetrakis(triphenylphosphine)palladium were dissolved in 50 mL of tetrahydrofuran (THF) under an argon atmosphere in a 100 mL round bottom flask having a thermometer, a reflux condenser, and an agitator, and 20 mL of 20% tetratriethylammonium hydroxide was added thereto. The resulting mixture was agitated at 75° C. for 24 hours.

When the reaction was complete, the reactant was cooled to room temperature and extracted several times with methylene chloride and washed with water. The washed reactant was treated with anhydrous magnesium sulfate to remove moisture. The remaining solid was filtered to remove the solvent. The resulting product was purified through a silica gel column with a methylene chloride solvent, providing 3.0 g of a white compound M-5 (yield: 56.8%).

Example 4

Synthesis of Compound M-6

Reaction Scheme 6

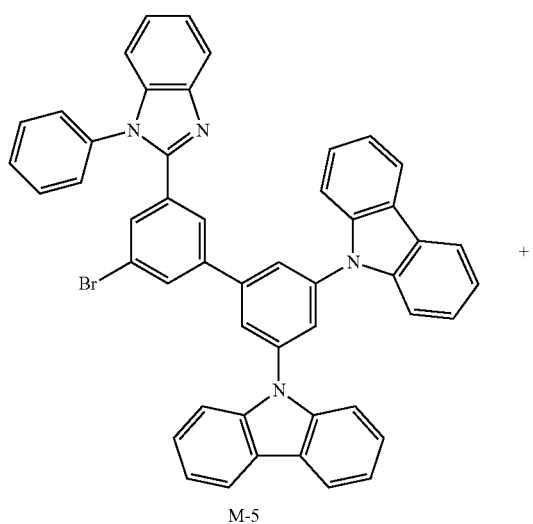

M-5

+

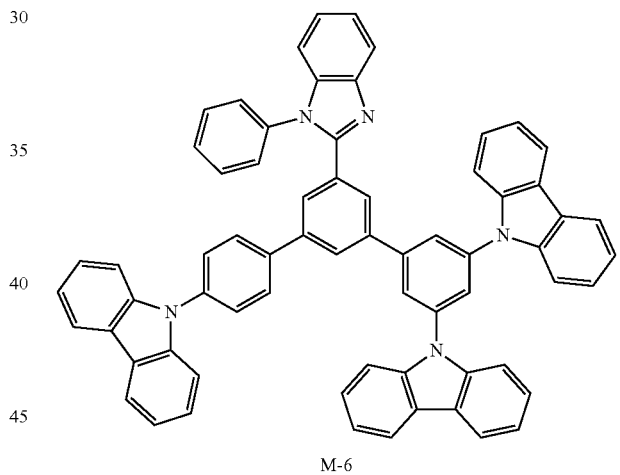

A

M-6

1.0 g (1.3 mmol) of compound M-5, 0.53 g (1.4 mmol) of a material A, and 0.15 g (0.16 mmol) of tetrakis(triphenylphosphine)palladium were dissolved in 30 mL of THF under an argon atmosphere in a 100 mL round bottom flask having a thermometer, a reflux condenser, and an agitator, and 15 mL of 20% tetratriethylammonium hydroxide was added thereto. The resulting mixture was agitated at 75° C. for 24 hours. When the reaction was complete, the reactant was cooled to room temperature and then extracted several times with methylene chloride and washed with water. The washed reactant was treated with anhydrous magnesium sulfate to remove moisture and then filtered to remove the solvent. The resulting product was purified through a silica gel column with a methylene chloride solvent, providing 1.0 g of a white compound M-6 (yield: 82.6%). When it was fabricated into a thin film, it had a maximum light emitting wavelength at 390 nm. It had an LC-MS theoretical value of $C_{67}H_{43}N_5$ $[MH]^+$ 918.3518 and a measurement value of 918.3604.

Example 5

Synthesis of Compound M-7

Reaction Scheme 7

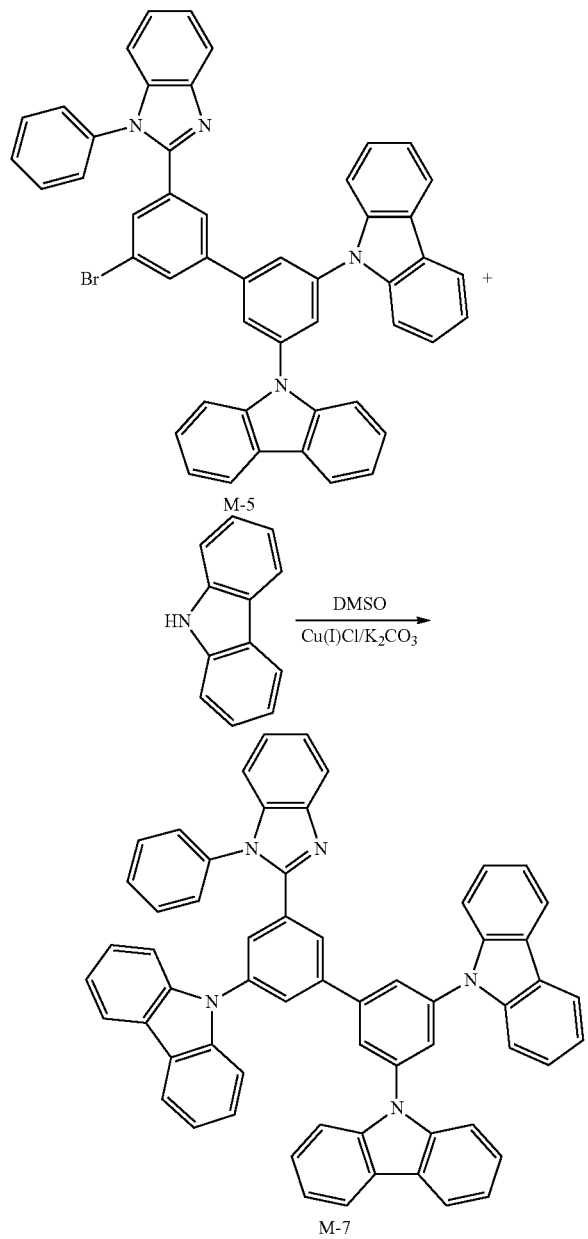

1.3 g (1.7 mmol) of M-5, 0.57 g (3.4 mmol) of carbazole, 0.08 g (0.86 mmol) of copper chloride, and 5.46 g (39 mmol) of potassium carbonate were dissolved in 30 mL of DMSO under an argon atmosphere in a 250 mL round bottom flask having a thermometer, a reflux condenser, and an agitator. The solution was agitated at 150° C. for 48 hours, and then cooled to room temperature and treated under reduced pressure to remove DMSO. The remaining solid was dissolved in methylene chloride, washed several times with water, treated with anhydrous magnesium sulfate to remove moisture, and then filtered to remove the solvent. The resulting product was purified through a silica gel column with a methylene chloride solvent, providing 0.66 g of a white compound M-7 (yield: 45.5%). When it was fabricated into a thin film, it had a maximum light emitting wavelength at 404 nm. Its LC-MS theoretical value was $C_{61}H_{39}N_5$ [MH]$^+$842.3205, and the measurement value was 842.3331.

Example 6

Synthesis of Compound M-8

Reaction Scheme 8

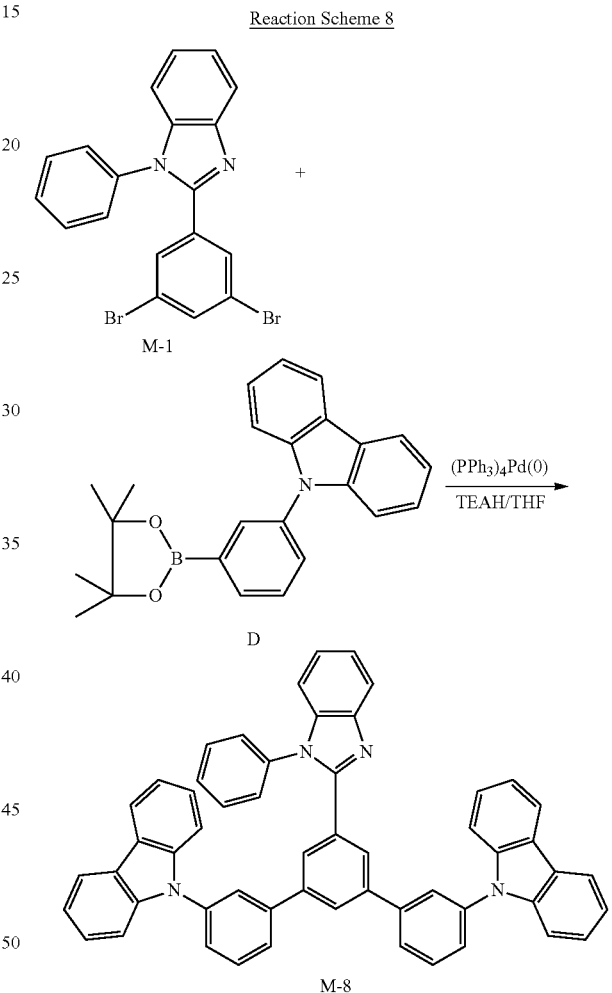

1.9 g (4.4 mmol) of compound M-1, 3.44 g (9.3 mmol) of a material D, and 0.4 g (0.34 mmol) of tetrakis(triphenylphosphine)palladium were dissolved in 30 mL of THF under an argon atmosphere in a 100 mL round bottom flask having a thermometer, a reflux condenser, and an agitator, and 15 mL of 20% tetratriethylammonium hydroxide was added thereto. The solution was agitated at 75° C. for 24 hours. When the reaction was complete, the reactant was cooled to room temperature and then extracted several times with methylene chloride and washed with water. The washed reactant was treated with anhydrous magnesium sulfate to remove moisture and filtered to remove the solvent. The resulting product was treated with a methylene chloride solvent through a silica gel column, providing 1.5 g of a white compound M-8 (yield: 44.9%). It had an LC-MS theoretical value of $C_{55}H_{36}N_4$ [MH]$^+$753.2940 and a measurement value of 753.2949.

Example 7

Synthesis of Compound M-9

Reaction Scheme 9

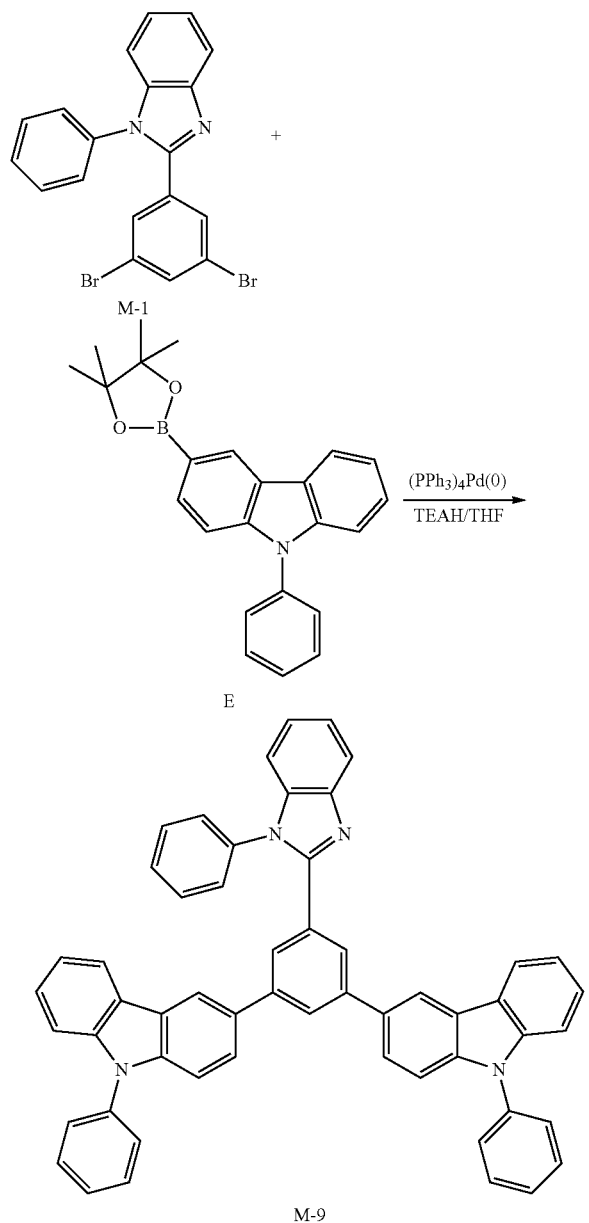

2.0 g (4.6 mmol) of compound M-1, 3.62 g (9.8 mmol) of a material E, and 0.4 g (0.34 mmol) of tetrakis(triphenylphosphine)palladium were dissolved in 30 mL of THF under an argon atmosphere in a 100 mL round bottom flask having a thermometer, a reflux condenser, and an agitator, and 15 mL of 20% tetratriethylammonium hydroxide was added thereto. The solution was agitated at 75° C. for 24 hours. When the reaction was complete, the reactant was cooled to room temperature and then extracted several times with methylene chloride and washed with water. The washed reactant was treated with anhydrous magnesium sulfate to remove moisture and filtered to remove the solvent. The remaining solid was purified with a methylene chloride solvent through a silica gel column, providing 1.6 g of a white compound M-9 (yield: 47.9%). It had a theoretical value of LC-MS $C_{55}H_{36}N_4$ [MH]$^+$753.2940 and a measurement value of 753.2980.

Analysis and Characteristic Measurement of Compounds

Figure 2:
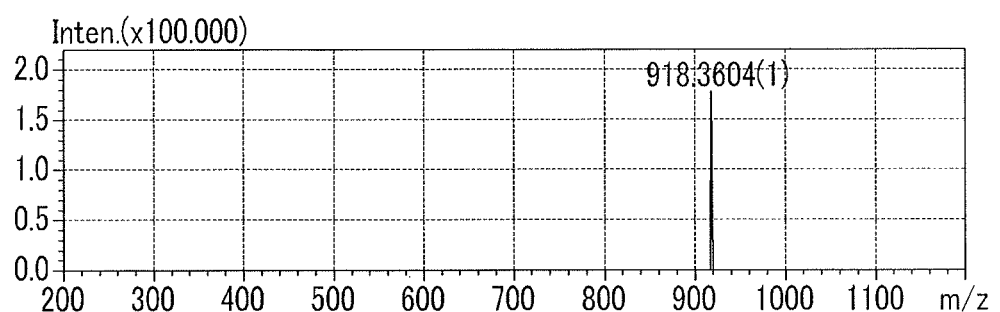
FIG. 2 illustrates LC-MS data of a compound M-6 prepared in Example 4.

The compounds (M-2 to M-4 and M-6 to M-9) of Examples 1 to 7 were measured regarding molecular weight to analyze the structure by using a liquid chromatography-mass analyzer (LC-MS, liquid chromatograph-mass spectrometry). LC-MS data of the compound M-6 prepared in Example 4 is shown in FIG. 2.

Figure 3:
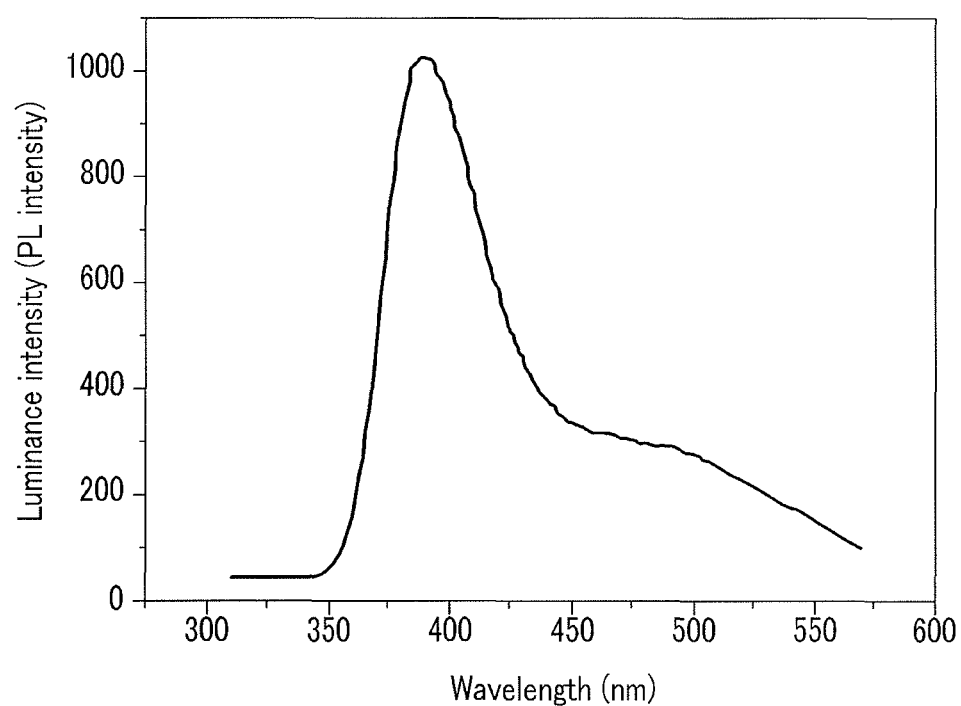
FIG. 3 illustrates a graph showing a photoluminescence (PL) wavelength of the compound M-6 prepared in Example 4.

The compounds (M-2 to M-4 and M-6 to M-9) of Examples 1 to 7 were also measured regarding photoluminescence (PL) wavelength by forming a thin film on a glass substrate and using a HITACHI F-4500 instrument to measure fluorescence characteristics. FIG. 3 illustrates the PL wavelength result of the compound M-6 according to Example 4. Referring to FIG. 3, when it was fabricated into a thin film, the compound M-6 had a maximum light emitting wavelength at 390 nm.

Fabrication of an Organic Photoelectric Device

Example 8

Device Fabrication Using a Solution Process

An ITO substrate was used as an anode. The anode was spin-coated, forming a poly(3,4-ethylenedioxy-thiophene) (PEDOT) layer on a top thereof. Next, a 400 Å thick emission layer was spin-coated on the surface of the PEDOT by doping compound M-6 of Example 4 (as a host) with about 13 wt % of Ir(mppy)$_3$ as a dopant. On the emission layer, BAlq was vacuum-deposited to a thickness of 50 Å to form a hole blocking layer. Then, Alq$_3$ was vacuum-deposited to a thickness of 200 Å on top of the emission layer to form an electron transport layer (ETL). On the electron transport layer (ETL), a 10 Å LiF layer and a 1,000 Å Al layer were sequentially vacuum-deposited to fabricate a cathode of the resultant organic photoelectric device.

The organic photoelectric device included a 5-component organic thin layer, and in particular, it was ITO 1,500 Å/PEDOT 600 Å/EML (M-6:Ir(mppy)$_3$) 400 Å/BAlq 50 Å/Alq$_3$ 200 Å/LiF 10 Å/Al 1,000 Å.

Comparative Example 1

Device Fabrication Using a Solution Process

According to Comparative Example, a device included ITO 1,500 Å/PEDOT 600 Å/EML (TCTA:TPBI 1:1, Ir(mppy)$_3$) 400 Å/BAlq 50 Å/Alq$_3$ 200 Å/LiF 10 Å/Al 1,000 Å.

Herein, the emission layer was spin-coated to a thickness of 400 Å by doping a mixture of 4,4',4"-tris(N-carbazolyl) triphenylamine (TCTA) and 2,2',2"-(1,3,5-benzenetriyl)tris (1-phenyl-1H-benzimidazole) (TPBI) prepared in a weight ratio of 1:1 as a host with about 13 wt % of Ir(mppy)$_3$ as a dopant.

A device using a solution process was fabricated according to the same method as in Example 8, except for the differences described above.

Example 9

Device Fabrication Using a Deposition Process

An ITO substrate was used as an anode, and a device was fabricated by vacuum-depositing a series of layers thereon.

ITO/DNTPD 600 Å/NPB 200 Å/M-4:Ir(ppy)$_3$, 7 wt % 300 Å/BCP 50 Å/Alq$_3$ 250 Å/LiF 10 Å/Al 1,000 Å

The device of Example 9 included a hole transport layer (HTL) formed by vacuum-depositing 4,4'-bis[N-[4-(N,N-di-m-tolylamino)phenyl]-N-phenylamino]biphenyl (DNTPD) and N-(1-naphthyl)-N-phenyl-amino]biphenyl (NPB) to respective thicknesses of 600 Å and 200 Å.

In addition, a 50 Å-thick 2,9-dimethyl-4,7-diphenyl-1,10-phenanthroline (BCP) layer was used to form a hole blocking layer. The device of Example 9 also included an emission layer formed to a thickness of 300 Å by vacuum-depositing compound M-4 of Example 3 as a host with about 7 wt % of Ir(ppy)$_3$ as a dopant.

Comparative Example 2

Device Fabrication Using Deposition Process

ITO/DNTPD 600 Å/NPB 200 Å/CBP:Ir(ppy)$_3$, 7 wt % 300 Å/CBP 50 Å/Alq$_3$ 250 Å/LiF 10 Å/Al 1,000 Å

According to Comparative Example 2, a device including an emission layer was formed by vacuum-depositing 4,4'-N,N'-dicarbazole-bipheyl (CBP) as a host and 7 wt % of Ir(ppy)$_3$ as a dopant to a thickness of 300 Å.

The device using a deposition process device was fabricated according the same method as in Example 9 except for the differences described above.

Performance Measurement of Organic Light Emitting Diodes

The organic light emitting diodes according to Examples 8 to 9 and Comparative Examples 1 and 2 were measured regarding current density and luminance change depending on voltage change and luminous efficiency change depending on luminance change. Specifically, they were measured as follows.

1) Current Density Change Depending on Voltage Change

Figure 4:
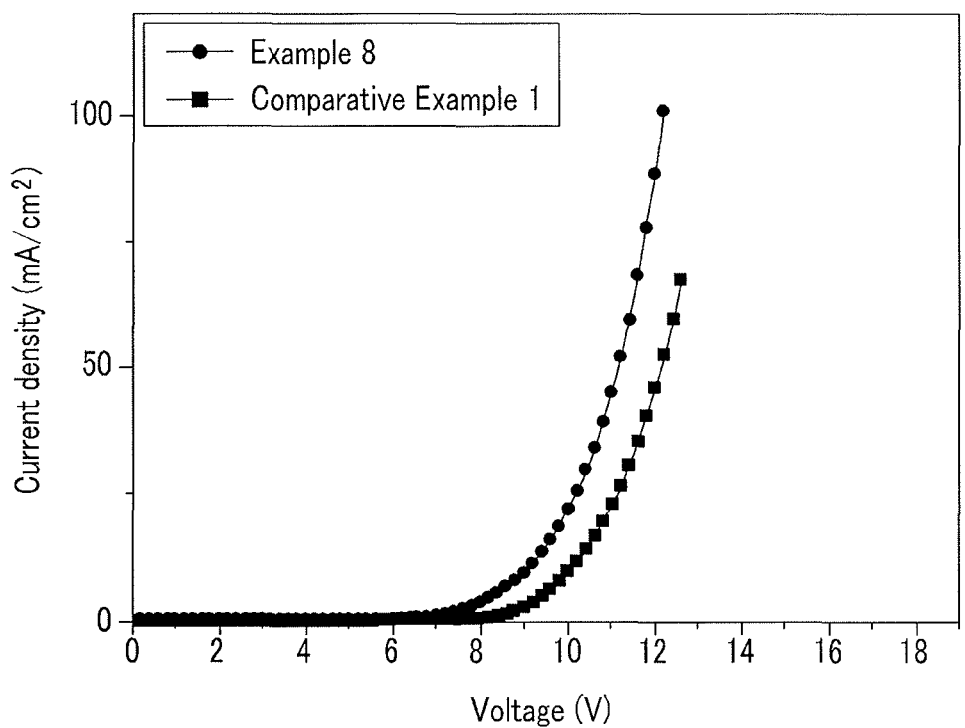
FIG. 4 illustrates a graph showing current density versus voltage of organic photoelectric devices fabricated using a solution process according to Example 8 and Comparative Example 1.
Figure 5:
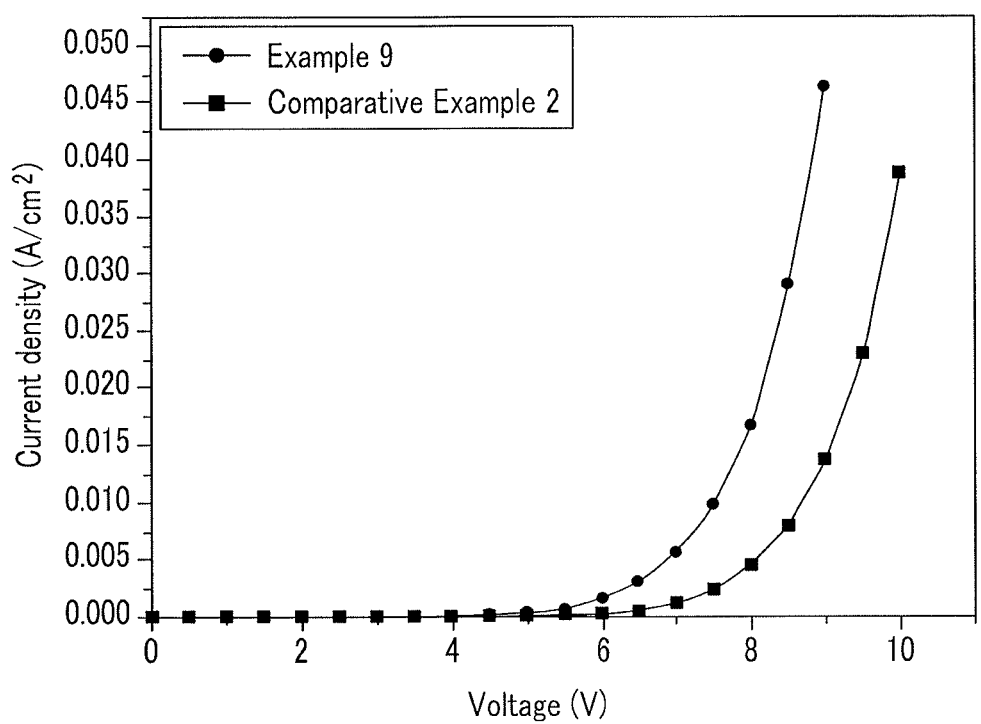
FIG. 5 illustrates a graph showing current density versus voltage of organic photoelectric devices fabricated using a solution process according to Example 9 and Comparative Example 2.

Each organic light emitting diode was measured regarding current value by using a current-voltage device (Keithley 2400) while its voltage was increased from 0. The current value was divided by area to calculate current density. The results are illustrated in FIGS. 4 and 5.

2) Luminance Change Depending on Voltage Change

Figure 6:
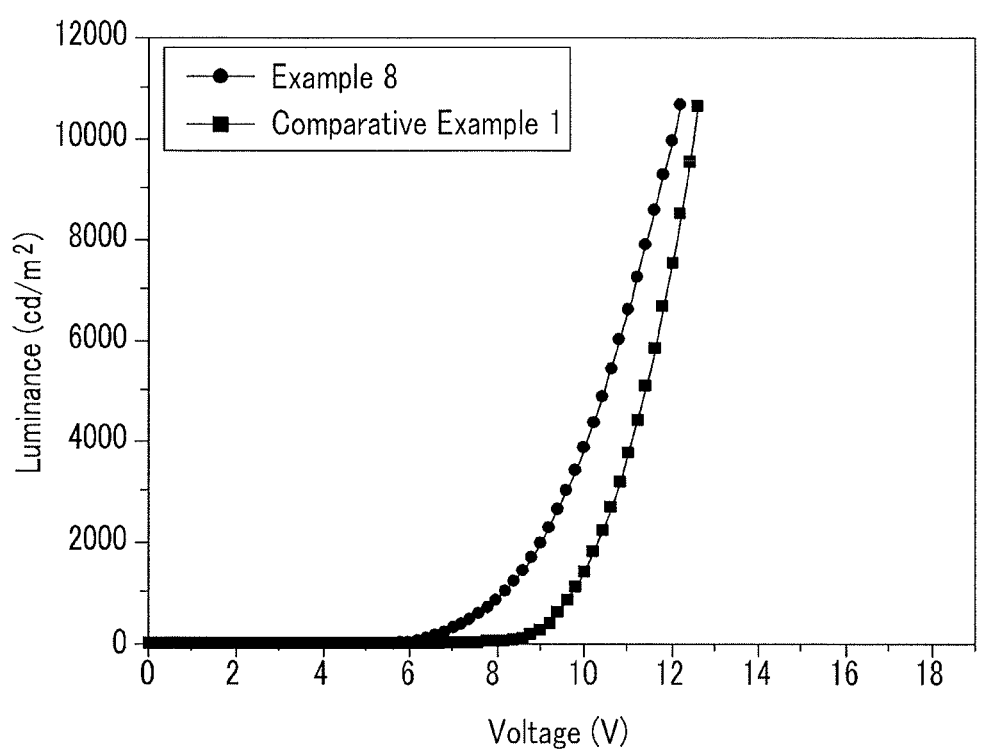
FIG. 6 illustrates a graph showing luminance versus voltage of organic photoelectric devices fabricated using a solution process according to Example 8 and Comparative Example 1.
Figure 7:
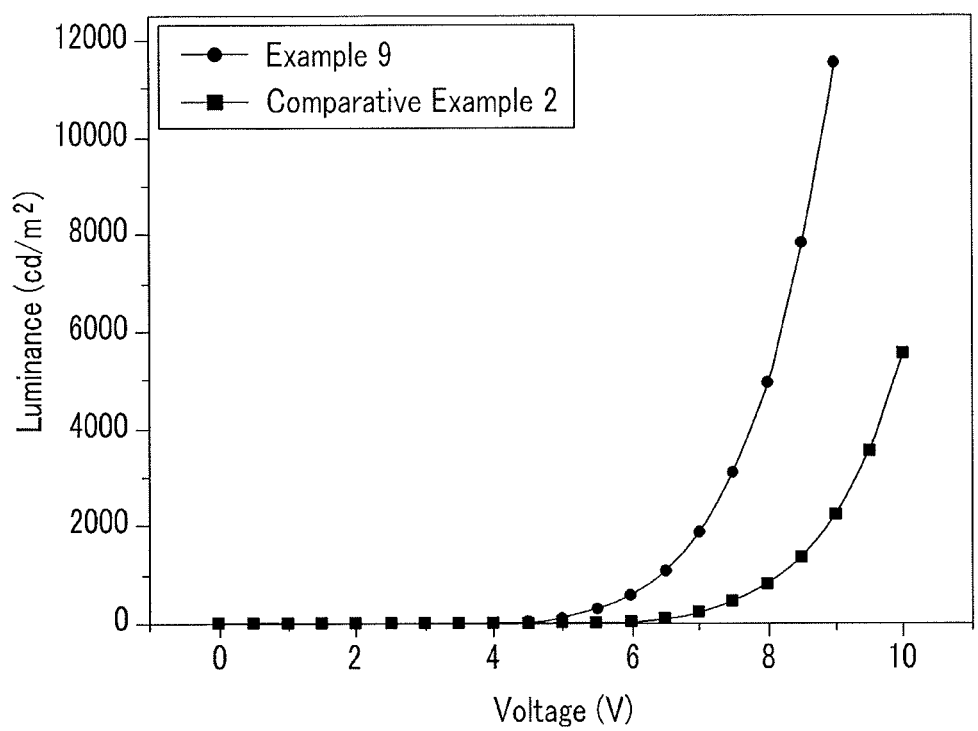
FIG. 7 illustrates a graph showing luminance versus voltage of organic photoelectric devices fabricated using a solution process according to Example 9 and Comparative Example 2.

The organic light emitting diodes were measured regarding luminance by using a luminance meter (Minolta Cs-1000A) while its voltage was increased from 0. The results are illustrated in FIGS. 6 and 7.

3) Luminous Efficiency Measurement Depending on Luminance Change

Figure 8:
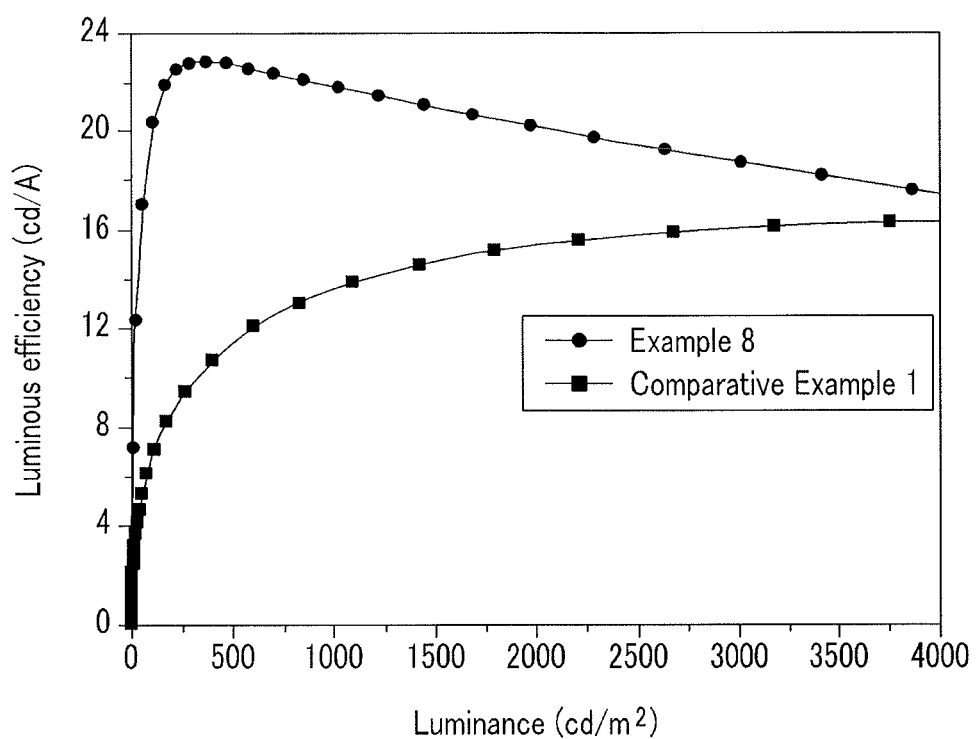
FIG. 8 illustrates a graph showing luminous efficiency versus luminance of organic photoelectric devices fabricated using a solution process according to Example 8 and Comparative Example 1.
Figure 9:
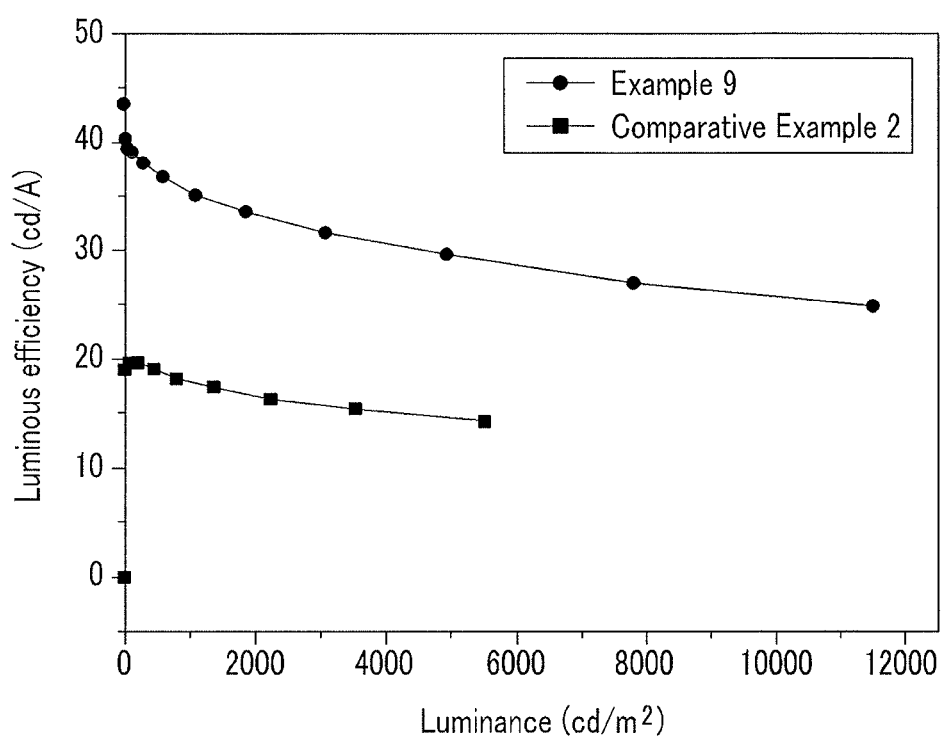
FIG. 9 illustrates a graph showing luminous efficiency versus luminance of organic photoelectric devices fabricated using a solution process according to Example 9 and Comparative Example 2.

The organic light emitting diodes were measured regarding luminous efficiency change depending on luminance change. The results are illustrated in FIGS. 8 and 9.

Tables 1 and 2 comprehensively show all the results. In particular, Table 1 shows performance evaluation results of the solution process devices according to Comparative Example 1 and Example 8.

TABLE 1

| | Emission layer material | at 1000 cd/m² Driving voltage (V) | at 1000 cd/m² Luminous efficiency (cd/A) | at 1000 cd/m² Luminous efficiency (lm/w) | Threshold voltage $V_{turn\ on}$ (V) | Max. luminous efficiency (cd/A) | Max. luminous efficiency (lm/W) |
|---|---|---|---|---|---|---|---|
| Comp. Ex. 1 | TCTA:TPBI (1:1) | 9.80 | 13.90 | 4.45 | 4.80 | 16.50 | 4.71 |
| Ex. 8 | M-6 | 8.2 | 21.7 | 8.3 | 4.0 | 22.8 | 10.4 |

Referring to Table 1 and FIGS. 4, 6, and 8, a benzimidazole compound according to an embodiment decreased the driving voltage of an organic light emitting diode and improved luminance and efficiency when included as a host material.

Table 2 shows performance evaluation results of the deposition process devices according to Comparative Example 2 and Example 9.

TABLE 2

| | Emission layer material | at 1000 cd/m² Driving voltage (V) | at 1000 cd/m² Luminous efficiency (cd/A) | at 1000 cd/m² Luminous efficiency (lm/w) | Threshold voltage $V_{turn\ on}$ (V) | Max. luminous efficiency (cd/A) | Max. luminous efficiency (lm/W) |
|---|---|---|---|---|---|---|---|
| Comp. Ex. 2 | CBP | 8.8 | 17.8 | 7.6 | 5 | 19.7 | 11.3 |
| Ex. 9 | M-4 | 7.0 | 35.4 | 19.3 | 3.5 | 43.5 | 43.2 |

Referring to Table 2 and FIGS. 5, 7, and 9, a benzimidazole compound according to an embodiment decreased the driving voltage of an organic light emitting diode and improved luminance and efficiency when included as a host material.

By way of summation and review, the efficiency and properties of the light emission diodes are dependent on the host material in the emission layer. Typical organic host materials may be exemplified by a material including naphthalene, anthracene, phenanthrene, tetracene, pyrene, benzopyrene, chrysene, pycene, carbazole, fluorene, biphenyl, terphenyl, triphenylene oxide, dihalobiphenyl, trans-stilbene, and 1,4-diphenylbutadiene.

The organic layer may have a structure in which a thin film (hole transport layer (HTL)) of a diamine derivative and a thin film of tris(8-hydroxy-quinolate)aluminum (Alq$_3$) are laminated. The Alq$_3$ thin film functions as an electron transporting emission layer.

The host material may typically include 4,4-N,N-dicarbazole biphenyl (CBP) having a glass transition temperature of 110° C. or less and high symmetry, and thus may crystallize and cause a short circuit and a pixel defect according to results of thermal resistance tests of the devices.

In addition, in host materials including CBP, the hole transporting property may be greater than the electron transporting property. In other words, as the injected hole transportation may be faster than the injected electron transportation, the excitons may be ineffectively formed in the emission layer. Therefore, the resultant device may exhibit deteriorated luminous efficiency.

Accordingly, the embodiments provide host materials, or charge transporting materials, e.g., electron transporting materials, hole blocking materials, and the like, that exhibit high thermal stability and triplet T1 energy.

The embodiments provide a benzimidazole compound exhibiting good charge transporting properties, good film stability, and high triplet T1 energy and thus may be applicable as host materials or charge transporting materials, e.g., electron transporting materials, hole blocking materials, and the like.

The benzimidazole compound of an embodiment may be applicable as host materials, electron transporting materials, or hole blocking materials, and thus may be used for an organic thin layer of an organic photoelectric device such as an organic emission layer, an electron transport layer (ETL), a hole blocking layer, and the like.

Thus, the embodiments provide benzimidazole compounds that have high solubility in an organic solvent and that are applicable as, e.g., a host material of an emission layer, an electron transporting material, or a hole blocking material, of an organic photoelectric device. For example, the benzimidazole compounds of an embodiment may emit fluorescence and phosphorescence at a red wavelength through a blue wavelength.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A benzimidazole compound represented by the following Chemical Formula 1:

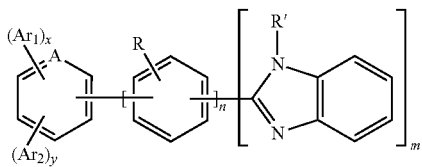

Chemical Formula 1 wherein, in Chemical Formula 1,

A is CR" or N wherein R" is hydrogen or a C1 to C10 alkyl,

Ar$_1$ to Ar$_2$ are each independently one selected from the group of a substituted or unsubstituted C6 to C30 arylamine, a substituted or unsubstituted C2 to C30 heteroarylamine, a substituted or unsubstituted carbazole, and a substituted or unsubstituted fluorene, x and y are each independently an integer of 1 to 5, provided that 2≤x+y≤5, R is hydrogen or a C1 to C7 alkyl, n is an integer of 0 to 3, R' is one selected from the group of a substituted or unsubstituted C1 to C50 alkyl and a substituted or unsubstituted C6 to C50 aryl, and m is 1 or 2.

2. The benzimidazole compound as claimed in claim 1, wherein R' in Chemical Formula 1 is a substituted or unsubstituted C6 to C50 aryl.

3. The benzimidazole compound as claimed in claim 1, wherein the benzimidazole compound represented by Chemical Formula 1 is represented by the following Chemical Formula 2:

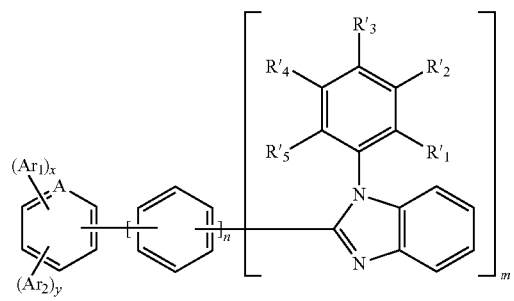

Chemical Formula 2 wherein, in Chemical Formula 2,

A is CR" or N wherein R" is hydrogen or a C1 to C10 alkyl,

Ar$_1$ to Ar$_2$ are each independently one selected from the group of a substituted or unsubstituted C6 to C30 arylamine, a substituted or unsubstituted C2 to C30 heteroarylamine, a substituted or unsubstituted carbazole, and a substituted or unsubstituted fluorene, x and y are each independently integers of 1 to 5, provided that 2≤x+y≤5, n is an integer of 0 to 3, R$_1$' to R$_5$' are each independently one selected from the group of hydrogen, a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, and m is 1 or 2.

4. The benzimidazole compound as claimed in claim 1, wherein $Ar_1$ to $Ar_2$ are each independently one selected from the group of a substituted or unsubstituted C6 to C30 arylamine and a substituted or unsubstituted carbazole.

5. The benzimidazole compound as claimed in claim 1, wherein:
one of $Ar_1$ and $Ar_2$ includes a substituted or unsubstituted C6 to C30 arylamine, and
another of $Ar_1$ and $Ar_2$ includes a substituted or unsubstituted carbazole.

6. The benzimidazole compound as claimed in claim 1, wherein $Ar_1$ to $Ar_2$ are each independently represented by one of the following Chemical Formulae 7, 24, 28, and 33:

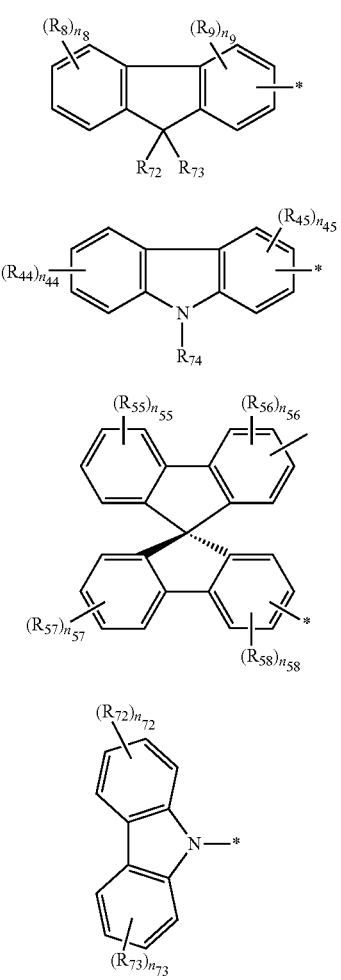

Chemical Formula 7

Chemical Formula 24

Chemical Formula 28

Chemical Formula 33 wherein, in Chemical Formulae 7, 24, 28, and 33,
$R_8$, $R_9$, $R_{44}$, $R_{45}$, $R_{55}$ to $R_{58}$, and $R_{72}$ to $R_{74}$ are each independently one selected from the group of a halogen, a cyano, a hydroxy, an amino, a nitro, a carboxyl, a substituted or unsubstituted C1 to C30 alkyl, a substituted or unsubstituted C1 to C20 alkenyl, a substituted or unsubstituted C6 to C30 aryl, a substituted or unsubstituted C2 to C30 heteroaryl, a substituted or unsubstituted C1 to C20 alkoxy, a substituted or unsubstituted C6 to C20 aryloxy, a substituted or unsubstituted C3 to C40 silyloxy, a substituted or unsubstituted C1 to C20 acyl, a substituted or unsubstituted C2 to C20 alkoxycarbonyl, a substituted or unsubstituted C2 to C20 acyloxy, a substituted or unsubstituted C2 to C20 heteroaryloxy, a substituted or unsubstituted C7 to C20 aryloxycarbonyl amino, a substituted or unsubstituted C1 to C20 sulfamoyl amino, a substituted or unsubstituted C1 to C20 sulfonyl, a substituted or unsubstituted C1 to C20 alkylthiol, a substituted or unsubstituted C6 to C20 arylthiol, a substituted or unsubstituted C1 to C20 heterocyclothiol, a substituted or unsubstituted C1 to C20 ureide, a substituted or unsubstituted C1 to C20 phosphoric acid amide, and a substituted or unsubstituted C3 to C40 silyl, $n_8$, $n_{44}$, $n_{55}$, $n_{57}$, $n_{72}$, and $n_{73}$ are each independently integers of 0 to 4, $n_9$, $n_{45}$, $n_{56}$, and $n_{58}$ are each independently integers of 0 to 3.

7. The benzimidazole compound as claimed in claim 1, wherein the benzimidazole compound is a charge transporting material or a host material in an organic photoelectric device.

8. The benzimidazole compound as claimed in claim 1, wherein the benzimidazole compound represented by Chemical Formula 1 is represented by one of the following Chemical Formulae 36 and 40:

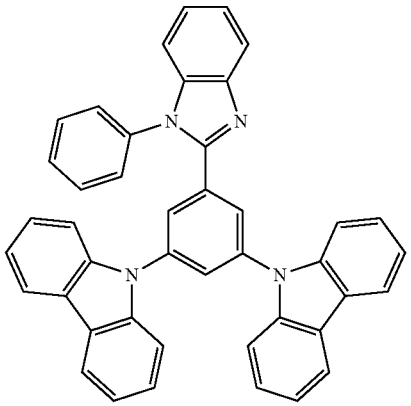

Chemical Formula 36

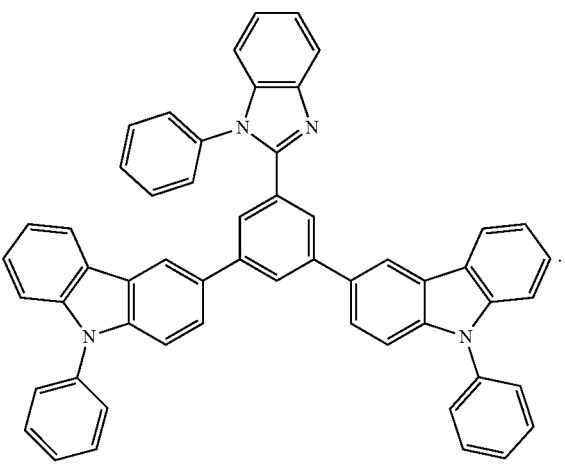

Chemical Formula 40

9. An organic photoelectric device, comprising:
an anode,
a cathode, and
at least one organic thin layer between the anode and cathode, the at least one organic thin layer including the benzimidazole compound as claimed in claim 1.

10. The organic photoelectric device as claimed in claim 9, wherein the at least one organic thin layer is an emission layer.

11. The organic photoelectric device as claimed in claim 9, wherein the at least one organic thin layer includes one or more of an electron injection layer (EIL), an electron transport layer (ETL), or a hole blocking layer.

12. A display element comprising the organic photoelectric device as claimed in claim 9.

* * * * *